(12) United States Patent
Cramail et al.

(10) Patent No.: US 9,695,269 B2
(45) Date of Patent: Jul. 4, 2017

(54) PREPARATION OF POLYURETHANES AND POLYESTERS FROM GLYCOLIPID TYPE COMPOUNDS

(71) Applicants: Henri Cramail, Sainte Terre (FR); Aurélie Boyer, Bordeaux (FR); Cédric Epoune Lingome, Amiens (FR); Carine Alfos, Pessac (FR); Benoit Gadenne, Chatel Guyon (FR); Eric Cloutet, Saint Caprais de Bordeaux (FR); Yves Queneau, Lyons (FR); Sylvie Moebs, Villieu (FR)

(72) Inventors: Henri Cramail, Sainte Terre (FR); Aurélie Boyer, Bordeaux (FR); Cédric Epoune Lingome, Amiens (FR); Carine Alfos, Pessac (FR); Benoit Gadenne, Chatel Guyon (FR); Eric Cloutet, Saint Caprais de Bordeaux (FR); Yves Queneau, Lyons (FR); Sylvie Moebs, Villieu (FR)

(73) Assignees: UNIVERSITÉ DE BORDEAUX (FR); INSTITUT DES CORPS GRAS ETUDES ET RECHERCHES TECHNIQUES—ITERG (FR); CENTRE NATIONAL DE LA RECHERCHE SCIENTIFIQUE (C.N.R.S) (FR); INSTITUT NATIONAL DES SCIENCES APPLIQUÉES LYON (FR)

(*) Notice: Subject to any disclaimer, the term of this patent is extended or adjusted under 35 U.S.C. 154(b) by 130 days.

(21) Appl. No.: 14/349,400

(22) PCT Filed: Oct. 2, 2012

(86) PCT No.: PCT/EP2012/069482
§ 371 (c)(1),
(2) Date: Apr. 3, 2014

(87) PCT Pub. No.: WO2013/050377
PCT Pub. Date: Apr. 11, 2013

(65) Prior Publication Data
US 2014/0235814 A1    Aug. 21, 2014

(30) Foreign Application Priority Data
Oct. 3, 2011   (FR) .................................... 11 58911

(51) Int. Cl.
*C08G 18/36*    (2006.01)
*C07H 13/04*    (2006.01)
*C08G 18/75*    (2006.01)

(52) U.S. Cl.
CPC ............. *C08G 18/36* (2013.01); *C07H 13/04* (2013.01); *C08G 18/755* (2013.01)

(58) Field of Classification Search
None
See application file for complete search history.

(56) References Cited

U.S. PATENT DOCUMENTS

| | | | | |
|---|---|---|---|---|
| 3,240,843 | A * | 3/1966 | Nelson | C08F 259/04 521/139 |
| 3,887,652 | A * | 6/1975 | Carrock | C08F 279/02 525/243 |
| 5,049,664 | A | 9/1991 | Yoshinaga et al. | |
| 8,912,149 | B1 * | 12/2014 | Rawat | A61K 47/48092 514/23 |
| 2006/0025379 | A1 * | 2/2006 | Hsieh-Wilson | A61K 31/737 514/54 |
| 2006/0177413 | A1 * | 8/2006 | Kalovidouris | A61K 31/715 424/78.3 |
| 2008/0254099 | A1 * | 10/2008 | Leroux | A23L 1/3084 424/439 |
| 2014/0235814 | A1 * | 8/2014 | Cramail | C07H 13/04 528/48 |

FOREIGN PATENT DOCUMENTS

| | | |
|---|---|---|
| DE | 1467705 A1 | 11/1969 |
| DE | 1518246 A1 | 12/1969 |
| JP | H03-047193 A | 2/1991 |

(Continued)

OTHER PUBLICATIONS

Synthesis and Aqueous Solution Properties of Novel Sugar Methacrylate Based Homopolymers and Block Copolymers, Narain et al.*

(Continued)

*Primary Examiner* — Peter A Salamon
(74) *Attorney, Agent, or Firm* — Ostrolenk Faber LLP

(57) ABSTRACT

The present invention relates to the use of a compound of formula (I):

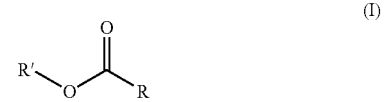

wherein:
R represents a linear or branched alkyl group, comprising from 3 to 27 carbon atoms, said alkyl group being substituted with at least two hydroxyl groups, and which may optionally contain one or more unsaturations; and
R' is selected from sugars or sugar-alcohols;
for preparing polyurethanes and polyesters.

28 Claims, No Drawings

(56) References Cited

FOREIGN PATENT DOCUMENTS

| | | |
|---|---|---|
| JP | H10-007693 A | 1/1998 |
| JP | H11-071391 A | 3/1999 |

OTHER PUBLICATIONS

International Search Report dated Oct. 30, 2012 issued in corresponding International patent application No. PCT/EP2012/069482.

Sharmila Muthukrishnan et al.: "Synthesis and Characterization of Methacrylate-Type Hyperbranched Glycopolymers via Self-Condensing Atom Transfer Radical Copolymerization", Marcomolecules, vol. 38, No. 8, Apr. 1, 2005, pp. 3108-3119, XP055027456.

Julien Bernard et al.: "Synthesis of Various Glycopolymer Architectures via Raft Polymerization: From Block Copolymers to Stars", Biomacromolecules, vol. 7, No. 1, Jan. 1, 2006, pp. 232-238, XP055027458.

Ravin Narain et al.: "Synthesis and Aqueous Solution Properties of Novel Sugar Methacrylate-Based Homopolymers and Block Copolymers", Biomacromolecues, vol. 4, No. 6, Nov. 1, 2003, XP055027459.

Notice of Reasons for Refusal dated Jul. 26, 2016 in corresponding Japanese Patent Application No. 2014-533862 (with English language translation)(8 total pages).

\* cited by examiner

PREPARATION OF POLYURETHANES AND POLYESTERS FROM GLYCOLIPID TYPE COMPOUNDS

CROSS REFERENCE TO RELATED APPLICATIONS

The present application is a 35 U.S.C. §371 National Phase conversion of PCT/EP2012/069482, filed Oct. 2, 2012, which claims benefit of French Application No. 11 58911, filed Oct. 3, 2011, the disclosure of which is incorporated herein by reference. The PCT International Application was published in the French language.

TECHNICAL FIELD OF THE INVENTION

The object of the present invention is novel polyurethanes and novel polyesters. The object of the present invention is also novel monomers as well as their preparation method and their use for synthesizing polyurethanes and polyesters.

BACKGROUND OF THE INVENTION

Most synthesized glycopolymers (polymers for which the structure includes saccharide groups) are derived from vinyl derivatives (Narain R. et al., *Eur. Polym. J.*, 2002, 38, 273-280), acrylic derivatives (Bernard, J. et al., *Biomacromolecules*, 2005, 7, p. 232-238; Barros M. T. et al., *Eur. Polym. J.*, 2009, 45, p. 295-301; Narain R. et al., *Biomacromolecules*, 2003, 4, p. 1746-1758) or acryloyl derivatives (Muthukrishnan, H. et al., *Macromolecules*, 2005, 38, p. 3108-3119) into which are incorporated pendant saccharide groups. Synthesis of linear polyurethanes derived from glycoside derivatives has not been much studied since it is difficult to obtain a monomer having a functionality of two, most sugars having more than four reactive alcohol functions. Moreover, several studies have dealt with the synthesis of polyurethanes stemming from fats. The latter have limited thermomechanical properties, such as a low glass transition temperature and low moduli.

Therefore, there exits a need for having available polyurethanes having improved thermo-mechanical properties compared to the polyurethanes derived from derivatives of fats.

The object of the present invention is to provide polyurethanes and polyesters having good thermo-mechanical properties, from derivatives of the glycolipid type.

The object of the present invention is also to provide novel monomers of the glycolipid type as well as their use for preparing polyurethanes and polyesters.

One of the objects of the present invention is to provide a method for preparing polyurethanes and polyesters, in linear form.

Another object of the present invention is to provide a method for preparing polyurethanes and polyesters in the form of a network.

Another object of the invention is to use the obtained polyurethanes and polyesters according to the invention for applications with high added value, notably in the medical and pharmaceutical field.

SUMMARY OF THE INVENTION

According to a first aspect, the present invention relates to the use of a compound of formula (I):

wherein:
R represents a linear or branched alkyl group comprising from 3 to 27 carbon atoms, preferably from 8 to 27 carbon atoms, said alkyl group being substituted with at least two hydroxyl groups, and which may optionally contain one or more unsaturations; and
R' is selected from sugars or sugar-alcohols;
for preparing polymers selected from polyurethanes and polyesters.

Preferably, the present invention relates to the use of a compound of formula (I) as defined above for preparing polyurethanes.

Within the scope of this invention, and unless mentioned otherwise, by <<sugar>>, is meant a carbohydrate selected from oses and asides, and comprising from 1 to 10 monosaccharide units. For example, by way of sugar according to the invention, are found threose, erythrose, desoxyribose, ribose, xylose, ribulose, lyxose, glucose, methyl glucoside, mannose, fructose, idose, sorbose, galactose, allose, maltose, lactose, isomaltose, isomaltulose, cellobiose, and saccharose, raffinose, melezitose. Osides include a linear or branched alkyl glycoside chain comprising from 1 to 12 carbon atoms. Preferably, the sugar according to the invention is selected from methyl glucoside and saccharose.

Within the scope of this invention, and unless indicated otherwise, by <<sugar-alcohol>>, is meant a sugar derivative as defined according to the invention, and comprising from 1 to 12 hydroxyl functions. A <<sugar-alcohol>> may notably be a sugar onto which is grafted a chain comprising one to more hydroxyl functions or a sugar, for which the reducing function has been hydrogenated. According to the invention, the term of <<sugar-alcohol>> may be assimilated with the term of <<sugar derivatives>>. For example, as a sugar-alcohol according to the invention, are found sorbitol, isomalt, xylitol, mannitol and arabinitol. Preferably, the sugar-alcohols according to the invention are selected from sorbitol and isomalt.

According to another aspect, the invention relates to compounds of formula (I):

wherein:
R represents a linear or branched alkyl group, comprising from 3 to 27 carbon atoms, preferably from 8 to 27 carbon atoms, said alkyl group being substituted with at least two hydroxyl groups, and which may optionally contain one or more unsaturations; and
R' is selected from sugars or sugar-alcohols.

DESCRIPTION OF EMBODIMENTS

According to an embodiment, R represents a linear or branched alkyl group comprising from 10 to 25 carbon atoms, preferably from 15 to 20 carbon atoms. In particular, R represents a linear or branched alkyl group, comprising 17 carbon atoms.

According to an embodiment, R represents a linear alkyl group.

According to an embodiment, R is substituted with at least two hydroxyl groups, preferably with 2 to 4 hydroxyl groups. Preferably, R is substituted with two hydroxyl groups.

According to an embodiment, R comprises an unsaturation.

According to an embodiment, the invention relates to the compounds of formula (I):

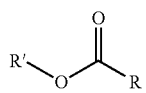

(I)

wherein:

R represents a linear or branched alkyl group, comprising from 8 to 27 carbon atoms, said alkyl group being substituted with at least two hydroxyl groups, and which may optionally contain an unsaturation; and R' is selected from sugars or sugar-alcohols.

According to an embodiment, the present invention relates to a compound of formula (I) as defined earlier, wherein R fits the formula (A):

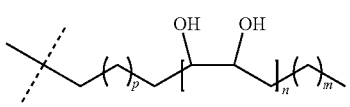

(A)

wherein:

n is an integer comprised from 1 to 3;

m is an integer comprised from 1 to 6;

p is an integer comprised from 1 to 9.

Within the scope of the invention, and unless indicated otherwise, the bond on which is found the symbol ⸺, means that said bond is connected to the carbon of the carbonyl function of the compound (I). Thus, within the scope of the invention, the compound of formula (I) may be written in the two following ways:

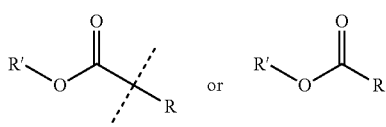

(I)

According to a particular embodiment, in the aforementioned formula (I), R fits the following formula (A-1):

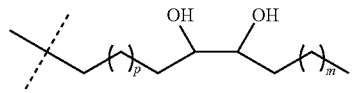

(A-1)

wherein:

m is an integer comprised from 1 to 6; and p is an integer comprised from 1 to 9.

The compounds of formula (I) for which R fits the formula (A-1) correspond to compounds of formula (I) wherein R fits the formula (A) and wherein n has the value 1.

Preferably, in the aforementioned formula (I), R fits the following formula (A-2):

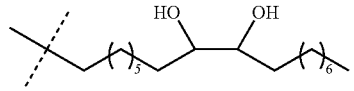

(A-2)

The compounds of formula (I) for which R fits the formula (A-2) correspond to compounds of formula (I) wherein R fits the formula (A) and wherein n has the value 1, p has the value 5 and m is equal to 6.

According to an embodiment, the present invention relates to a compound of formula (I) as defined earlier, wherein R' is selected from the group consisting of threose, erythrose, deoxyribose, ribose, xylose, ribulose, lyxose, glucose, methyl glucoside, mannose, fructose, idose, sorbose, galactose, allose, maltose, lactose, isomaltose, isomaltulose, cellobiose, saccharose, raffinose, melezitose, sorbitol, isomalt, xylitol, mannitol and arabinitol.

According to an embodiment, R' is selected from the group consisting of threose, erythrose, deoxyribose, ribose, xylose, ribulose, lyxose, methyl glucoside, idose, galactose, allose, maltose, lactose, isomaltose, isomaltulose, cellobiose, saccharose, raffinose, melezitose, sorbitol, isomalt, xylitol and arabinitol.

Preferentially, R' is selected from the group consisting of sorbitol, isomalt, methyl glucoside and saccharose.

According to a particular embodiment, the present invention relates to the compounds of formula (I), characterized in that R' fits the following formula (B):

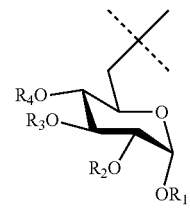

(B)

wherein $R_1$, $R_2$, $R_3$ and $R_4$ represent, independently of each other: H; an alkyl group comprising from 1 to 12 carbon atoms; a group $CH_3C(O)-$; an arylalkyl group comprising from 6 to 12 carbon atoms; a group $((C_1-C_6)$ alkyl$)_3$-Si— or $R_1$ and $R_2$, $R_2$ and $R_3$, or $R_3$ and $R_4$, form together an isopropylidene group.

Preferably, $R_1$, $R_2$, $R_3$ and $R_4$ are independently of each other selected from H and an alkyl group comprising from 1 to 12 carbon atoms.

According to the invention, preferred compounds are those for which $R_1$ represents a methyl, and $R_2$, $R_3$ and $R_4$ represent H.

The present invention may also relate to the compounds of formula (I) wherein R' may fit the formula (B'):

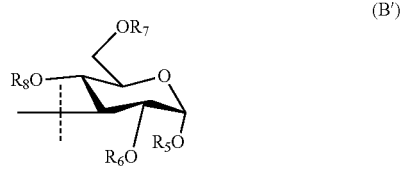

(B')

wherein $R_5$, $R_6$, $R_7$ and $R_8$ represent, independently of each other: H; an alkyl group comprising from 1 to 12 carbon atoms; a group $CH_3C(O)$—; an arylalkyl group comprising from 6 to 12 carbon atoms; a group $((C_1-C_6)\text{alkyl})_3\text{-Si}$— or $R_5$ and $R_6$ or $R_7$ and $R_8$, form together an isopropylidene group.

Preferably, $R_5$, $R_6$, $R_7$ and $R_8$ are independently of each other selected from H and an alkyl group comprising from 1 to 12 carbon atoms.

According to the invention, preferred compounds are those for which $R_5$ represents a methyl, and $R_6$, $R_7$ and $R_8$ represent H.

According to another embodiment, the present invention relates to the compound of formula (I) for which R' fits the formula (C):

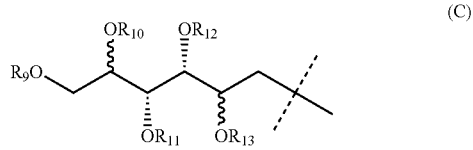

(C)

wherein $R_9$, $R_{10}$, $R_{11}$, $R_{12}$ and $R_{13}$ represent, independently of each other: H; an alkyl group comprising from 1 to 12 carbon atoms; a group $CH_3C(O)$—; an arylalkyl group comprising from 6 to 12 carbon atoms; a group $((C_1-C_6)\text{alkyl})_3\text{-Si}$— or $R_9$ and $R_{10}$, or $R_{10}$ and $R_{11}$, or $R_{11}$ and $R_{12}$, or $R_{12}$ and $R_{13}$, form together an isopropylidene group.

Preferably, $R_9$, $R_{10}$, $R_{11}$, $R_{12}$ and $R_{13}$ are independently of each other selected from H and an alkyl group comprising from 1 to 12 carbon atoms.

Preferred compounds of the aforementioned formula (I), are those for which R' fits any of the following formulae:

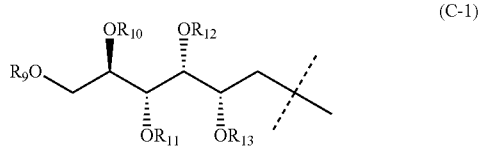

(C-1)

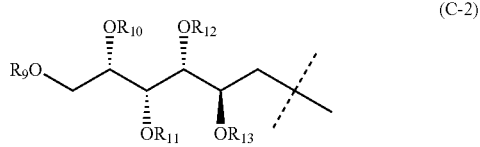

(C-2)

According to the invention, preferred compounds are those for which $R_9$, $R_{10}$, $R_{11}$, $R_{12}$ and $R_{13}$ represent H.

Within the scope of the invention, and unless specified otherwise, ~~~ represents a bond which may be in front or behind the plane formed by the main aliphatic chain.

According to another embodiment, the present invention relates to compounds of formula (I) for which R' fits the following formula (D):

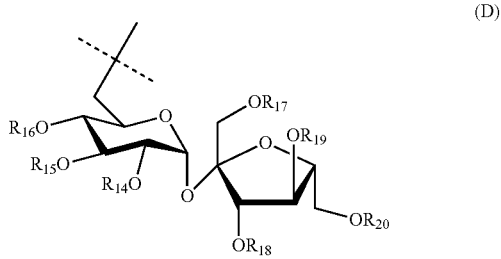

(D)

wherein $R_{14}$, $R_{15}$, $R_{16}$, $R_{17}$, $R_{18}$, $R_{19}$ and $R_{20}$ represent, independently of each other: H; an alkyl group comprising from 1 to 12 carbon atoms; a group $CH_3C(O)$—; an arylalkyl group comprising from 6 to 12 carbon atoms; a group $((C_1-C_6)\text{alkyl})_3\text{-Si}$— or $R_{14}$ and $R_{17}$ or $R_{19}$ and $R_{20}$ form together an isopropylidene group.

Preferably, $R_{14}$, $R_{15}$, $R_{16}$, $R_{17}$, $R_{18}$, $R_{19}$ and $R_{20}$ are independently of each other selected from H and an alkyl group comprising from 1 to 12 carbon atoms.

According to the invention, preferred compounds are those for which $R_{14}$, $R_{15}$, $R_{16}$, $R_{17}$, $R_{18}$, $R_{19}$ and $R_{20}$ represent H.

According to another embodiment, the present invention relates to the compounds of formula (I) for which R' fits the following formula (D'):

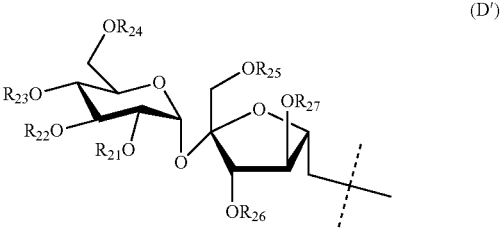

(D')

wherein $R_{21}$, $R_{22}$, $R_{23}$, $R_{24}$, $R_{25}$, $R_{26}$ and $R_{27}$ represent, independently of each other: H; an alkyl group comprising from 1 to 12 carbon atoms; a group $CH_3C(O)$—; an arylalkyl group comprising from 6 to 12 carbon atoms; a group $((C1-C6)\text{alkyl})_3\text{-Si}$— or $R_{23}$ and $R_{24}$ or $R_{21}$ and $R_{25}$ or $R_{26}$ and $R_{27}$ form together an isopropylidene group.

Preferably, $R_{21}$, $R_{22}$, $R_{23}$, $R_{24}$, $R_{25}$, $R_{26}$ and $R_{27}$ are independently of each other selected from H and an alkyl group comprising from 1 to 12 carbon atoms.

According to the invention, preferred compounds are those for which $R_{21}$, $R_{22}$, $R_{23}$, $R_{24}$, $R_{25}$, $R_{26}$ and $R_{27}$ represent H.

According to another embodiment, the present invention relates to the compounds of formula (I) for which R' fits the following formula (E):

(E)

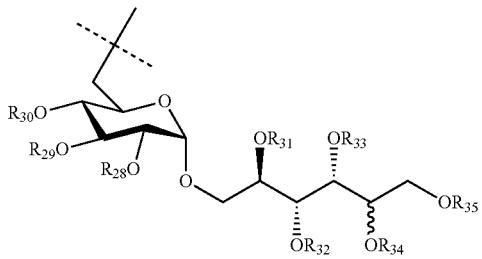

wherein $R_{28}$, $R_{29}$, $R_{30}$, $R_{31}$, $R_{32}$, $R_{33}$, $R_{34}$ and $R_{35}$ represent, independently of each other: H; an alkyl group comprising from 1 to 12 carbon atoms; a group $CH_3C(O)$—; an arylalkyl group comprising from 6 to 12 carbon atoms; a group $((C_1-C_6)alkyl)_3$-Si— or $R_{29}$ and $R_{30}$ or $R_{31}$ and $R_{32}$ or $R_{32}$ and $R_{33}$ or $R_{33}$ and $R_{34}$ form together an isopropylidene group.

Preferably, $R_{28}$, $R_{29}$, $R_{30}$, $R_{31}$, $R_{32}$, $R_{33}$, $R_{34}$ and $R_{35}$ are independently of each other selected from H and an alkyl group comprising from 1 to 12 carbon atoms.

According to the invention, preferred compounds are those for which $R_{28}$, $R_{29}$, $R_{30}$, $R_{31}$, $R_{32}$, $R_{33}$, $R_{34}$ and $R_{35}$ represent H.

According to another embodiment, the present invention relates to the compounds of formula (I) for which R' fits the following formula (E'):

(E')

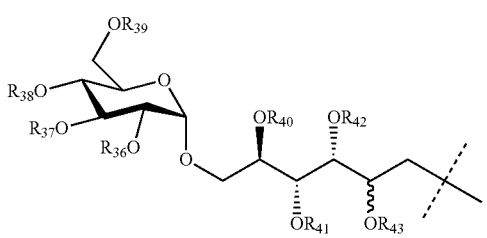

wherein $R_{36}$, $R_{37}$, $R_{38}$, $R_{39}$, $R_{40}$, $R_{41}$, $R_{42}$ and $R_{43}$ represent, independently of each other: H; an alkyl group comprising from 1 to 12 carbon atoms; a group $CH_3C(O)$—; an arylalkyl group comprising from 6 to 12 carbon atoms; a group $((C_1-C_6)alkyl)_3$-Si— or $R_{37}$ and $R_{38}$ or $R_{38}$ and $R_{39}$ or $R_{40}$ and $R_{41}$ or $R_{41}$ and $R_{42}$, or $R_{42}$ and $R_{43}$ form together an isopropylidene group.

Preferably, $R_{36}$, $R_{37}$, $R_{38}$, $R_{39}$, $R_{40}$, $R_{41}$, $R_{42}$ and $R_{43}$ are independently of each other selected from H and an alkyl group comprising from 1 to 12 carbon atoms.

Preferred compounds of the aforementioned formula (I) are those for which R' fits the following formula:

(E'-1)

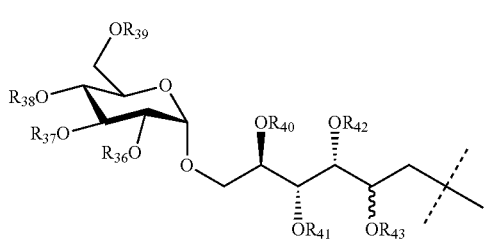

According to the invention, preferred compounds are those for which $R_{36}$, $R_{37}$, $R_{38}$, $R_{39}$, $R_{40}$, $R_{41}$, $R_{42}$ and $R_{43}$ represent H.

According to the invention, the groups $R_1$ to $R_{43}$ may represent any known group for protecting hydroxyl functions of sugars, notably an —$SO_2$—($C_6$-$C_{10}$) aryl group or an —$SO_2$—($C_1$-$C_6$) alkyl group.

The inventors have advantageously prepared novel glycosylated monomers derived from renewable resources.

Within the scope of the invention, and unless indicated otherwise, the term of <<glycosylated monomer>> or <<glycosylated synthon>> represents a bio-sourced polyol monomer derived from the condensation of a hydroxylated fatty chain with a derivative containing one or more sugar units. Among fatty chains, mention may be made of the chains derived from oleic acid, palmitoleic acid, linoleic acid, linolenic acid, erucic acid or ricinoleic acid.

The glycosylated monomers according to the invention are also called <<glycolipid derivatives>> or <<glycolipid derivatives>>, since they derive both from a fatty chain and from sugars.

The compounds of the aforementioned formula (I) therefore include both a <<fatty chain>> portion and a <<sugar>> portion within their structure, which each comprise from one to more alcohol functions.

The structures of these bio-sourced polyols according to the invention proved to be very interesting because of the multiple alcohol functions present on said polyols, which make them potential precursors of networks of polymers, and notably networks of polyurethanes. These monomers are advantageously functional precursors with a controlled functionality.

Moreover, the purity of the monomers is significant since it may allow optimization of the properties of the polymers obtained according to the invention.

The compounds of the aforementioned formula (I) may be used as surfactants.

Among "alkyl" radicals, mention may notably be made, when they are linear, of the methyl, ethyl, propyl, butyl, pentyl, hexyl, octyl, nonyl and decyl radicals. Mention may notably be made, when they are branched or substituted with one or more alkyl radicals, of isopropyl, tert-butyl, 2-ethylhexyl, 2-methylbutyl, 2-methylpentyl, 1-methylpentyl and 3-methylheptyl radicals.

According to the present invention, the "alkylene" radicals represent radicals (also called alkylidenes) derived from alkanes for which the two terminal hydrogen atoms have been suppressed. When said alkylene radicals are linear, they may be represented by the formula —$(CH_2)_k$—, k corresponding to the number of carbon atoms of the alkane from which stems the alkylene radical.

According to the present invention, the <<aryl>> radicals represent hydrocarbon mono- or bi-cycles comprising from 6 to 14 carbon atoms, optionally substituted, mention may notably be made of phenyl or anthracene.

According to the present invention, by <<cycloalkylene>> radicals are meant radicals derived from cycloalkanes for which one terminal hydrogen atom has been suppressed. According to the invention, the cycloalkylene radicals may be substituted with one or more ($C_1$-$C_6$) alkyl groups.

Within the scope of the invention, and unless indicated otherwise, by ($C_1$-$C_6$) alkyl is meant an alkyl group comprising from 1 to 6 carbon atoms.

Within the scope of the invention, and unless indicated otherwise, by ($C_6$-$C_{10}$) aryl is meant an aryl group comprising from 6 to 10 carbon atoms.

The expression "arylene" refers to a radical (also called arenediyl) derived from arenes for which two hydrogen atoms of the ring have been suppressed. Among arylene radicals, mention may for example be made of the o-phenylene or benzene-1,2-diyl radicals.

According to the present invention, the <<arylalkyl>> radicals represent an alkyl radical substituted with an aryl group. The arylalkyl radicals are aryl-alkyl-radicals, the aryl and alkyl groups being as defined above. Among arylalkyl radicals, mention may notably be made of the benzyl or phenethyl radicals. These arylalkyl groups may be substituted with one or more substituents selected from amino, hydroxy groups, a halogen, alkyl or alkoxy groups.

According to the invention, the <<cycloalkyl>> radical represents any mono- or bi-cyclic non-aromatic group containing from 4 to 10 carbon atoms. Mention may notably be made of cyclobutyl, cyclopentyl, cyclohexyl, cycloheptyl, cyclooctyl.

According to another aspect, the present invention relates to a polymer which may be obtained by polymerization of a compound of formula (I) as defined earlier and of a (poly)isocyanate. The polymer obtained according to this embodiment is a homopolymer of the polyurethane type.

According to another aspect, the present invention relates to a polyester which may be obtained by reaction of a compound of formula (I) as defined earlier with an acid di-chloride for example.

According to an embodiment, the (poly)isocyanate used according to the invention may be a diisocyanate fitting the formula (O)CN-$A_3$-NC(O), wherein $A_3$ represents:

a linear or branched alkylene group comprising from 2 to 20 carbon atoms; or a cycloalkylene-alkylene-cycloalkylene group, comprising from 6 to 30 carbon atoms; or an arylene-alkylene-arylene group, comprising from 6 to 30 carbon atoms; or a cycloalkylene group, comprising from 3 to 10 carbon atoms;

an alkylene-cycloalkylene group, comprising from 3 to 15 carbon atoms; or an arylene group comprising from 6 to 10 carbon atoms.

Preferably, the diisocyanate is selected from the group consisting of: 1,6-hexamethylene diisocyanate (HDI), 1,12-dodecane diisocyanate, cyclobutane 1,3-diisocyanate, cyclohexane 1,3 and/or 1,4-diisocyanate, 1-isocyanato 3,3,5-trimethyl-5-diisocyanato-methyl cyclohexane (IPDI), 1,3- and/or 1,4-phenylene diisocyanate, 2,4- and/or 2,6-toluoylene diisocyanate, diphenylmethane 4,4'-diisocyanate (MDI), 1,3-bis-isocyanatomethyl cyclohexane and methylene-bis (4-cyclohexylisocyanate).

Preferably, the diisocyanate is 1-isocyanato 3,3,5-trimethyl-5-diisocyanato-methyl cyclohexane (IPDI).

According to a particular embodiment, a polymer which may be obtained by polymerisation of a compound (I) and of a (poly)isocyanate as defined earlier, fits the following formula (IV):

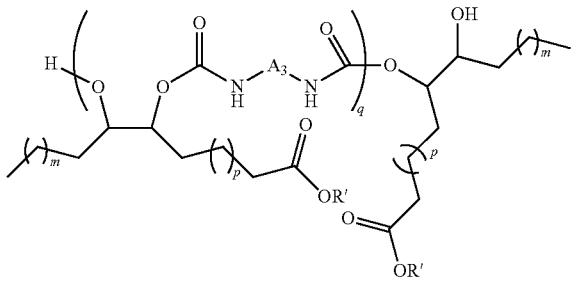

(IV)

wherein:
n is 1;
m is comprised from 1 to 6;
p is comprised from 1 to 9;
R' is selected from sugars or sugar-alcohols;
$A_3$ is selected from the group consisting of:
   a linear or branched alkylene group comprising from 2 to 20 carbon atoms;
   a cycloalkylene-alkylene-cycloalkylene group comprising from 6 to 30 carbon atoms;
   an arylene-alkylene-arylene group, comprising from 6 to 30 carbon atoms;
   a cycloalkylene group, comprising from 3 to 10 carbon atoms;
   an alkylene-cycloalkylene group, comprising from 3 to 15 carbon atoms; and
   an arylene group comprising from 6 to 10 carbon atoms;
q represents an integer comprised from 2 to 500,000, preferably from 2 to 50,000, notably from 2 to 5000, preferably from 2 to 500 and preferentially from 2 to 50.

Preferentially, the polymer which may be obtained by polymerization of a compound (I) and of IPDI, as a (poly)isocyanate as defined earlier, fits the following formula (IV-1):

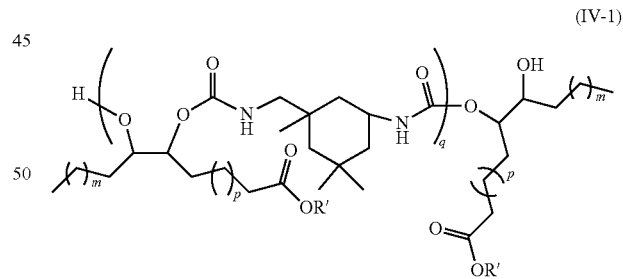

(IV-1)

In particular, in the aforementioned formula (IV-1), m has the value 6 and p has the value 5.

Preferred polymers according to the invention, are those for which in the aforementioned formulae (IV) or (IV-1), R' fits the formula (B) as defined earlier. Preferably, in formula (B), $R_1$ represents a methyl and $R_2$, $R_3$ and $R_4$ represent H.

Preferred polymers according to the invention are those for which in the aforementioned formulae (IV) or (IV-1), R' fits the formula (B') as defined earlier. Preferably, in formula (B'), $R_5$ represents a methyl and $R_6$, $R_7$ and $R_8$ represent H.

Preferred polymers according to the invention are those for which in the aforementioned formulae (IV) or (IV-1), R' fits the formula (C) as defined earlier. Preferably, in formula (C), $R_9$, $R_{10}$, $R_{11}$, $R_{12}$ and $R_{13}$ represent H.

Preferred polymers according to the invention are those for which in the aforementioned formulae (IV) or (IV-1), R' fits the formula (D) as defined earlier. Preferably, in formula (D), $R_{14}$, $R_{15}$, $R_{16}$, $R_{17}$, $R_{18}$, $R_{19}$ and $R_{20}$ represent H.

Preferred polymers according to the invention are those for which in the aforementioned formulae (IV) or (IV-1), R' fits the formula (D') as defined earlier. Preferably, in formula (D'), $R_{20}$, $R_{21}$, $R_{22}$, $R_{23}$, $R_{24}$, $R_{25}$, $R_{26}$ and $R_{27}$ represent H.

Preferred polymers according to the invention are those for which in the aforementioned formulae (IV) or (IV-1), R' fits the formula (E) as defined earlier. Preferably in formula (E), $R_{28}$, $R_{29}$, $R_{30}$, $R_{31}$, $R_{32}$, $R_{33}$, $R_{34}$ and $R_{35}$ represent H.

Preferred polymers according to the invention are those for which in the aforementioned formulae (IV) or (IV-1), R' fits the formula (E') as defined earlier. Preferably, in formula (E'), $R_{36}$, $R_{37}$, $R_{38}$, $R_{39}$, $R_{40}$, $R_{41}$, $R_{42}$ and $R_{43}$ represent H.

According to another aspect, the present invention relates to a polymer which may be obtained by polymerization of a compound (I) as defined earlier, of a (poly)isocyanate and of a diol.

According to an embodiment, the present invention relates to a polymer which may be obtained by polymerization of a compound (I) as defined earlier, of a (poly) isocyanate and of a diol selected from alkane-diols, polyalkylene-diols, polyether-diols, polyester-diols and diols having one of the following formulae:

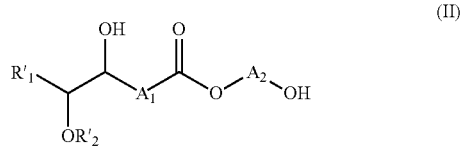

(II)

wherein:
$R'_1$ represents a linear or branched alkyl group, comprising from 2 to 14 carbon atoms;
$R'_2$ represents a linear or branched alkyl group, comprising from 1 to 8 carbon atoms;
$A_1$ represents a linear or branched divalent alkylene radical comprising from 2 to 14 carbon atoms;
$A_2$ represents a linear or branched divalent alkylene radical comprising from 1 to 10 carbon atoms;

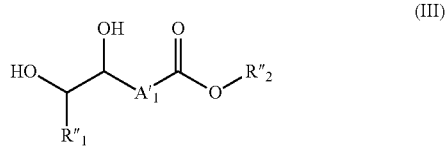

(III)

and
wherein:
$R''_1$ represents a linear or branched alkyl group, comprising from 2 to 14 carbon atoms;
$R''_2$ represents a linear or branched alkyl group, comprising from 1 to 8 carbon atoms;
$A'_1$ represents a linear or branched divalent alkylene radical, comprising from 2 to 14 carbon atoms.

The polymers obtained according to this embodiment represent a co-polymer of the polyurethane type.

Among alkane-diols, mention may for example be made of ethane-diol, propane-diol, butane-diol, pentane-diol, hexane-diol, heptane-diol, octane-diol, decane-diol or dodecane-diol.

Among polyalkylene-diols, mention may for example be made of polypropylene-glycol, polyethylene-glycol.

In particular, the present invention relates to a polymer which may be obtained by polymerization of a compound (I) as defined earlier, of a (poly)isocyanate and of a diol of formula (III).

Preferably, in the diol of the aforementioned formula (III), $R''_1$ represents an octyl group, $R''_2$ represents an ethyl group and $A'_1$ represents a heptylene radical.

In particular, the present invention relates to a polymer which may be obtained by polymerization of a compound (I) as defined earlier, of a (poly)isocyanate and of a diol of formula (II).

Preferably, in the diol of the aforementioned formula (II), $R'_1$ represents an octyl group, $R'_2$ represents an ethyl group, $A_1$ represents a heptylene radical and $A'_2$ represents a pentylene radical.

According to the embodiment, the (poly)isocyanate allowing preparation of the polymer according to the invention is a diisocyanate fitting the formula (O)CN-$A_3$-NC(O), wherein $A_3$ is as defined earlier.

According to another aspect, the invention relates to a method for preparing a polyurethane, comprising a step for reacting a compound of formula (I) as defined above, with a diisocyanate of formula (O)CN-$A_3$-NC(O) as defined earlier, at a temperature comprised from 40° C. to 100° C., preferably at 60° C., in a solvent.

Typically, the reaction may be carried out in the presence of a catalyst with an amount comprised from 0.01 to 0.9% by mass based on the total mass of reagents. Preferably, the catalyst used is di-butyltin dilaurate at an amount comprised from 0.02 to 0.1% by mass.

The formation of the polyurethanes according to the invention may be confirmed by FTIR (infrared spectroscopy) by the disappearance of the vibration band of the isocyanate functions at 2,250 cm$^{-1}$ as well as the appearance of one of the urethane functions localized at 1,530 cm$^{-1}$. The reaction may be considered as completed when the vibration band of the isocyanate functions no longer changes over time.

According to another aspect, the present invention relates to a copolymer which may be obtained by polymerization of at least two different compounds of formula (I) and of a (poly)isocyanate as defined earlier. In particular, the copolymer is obtained from two different compounds of formula (I) and from a (poly)isocyanate as defined earlier.

According to the nature of the solvent used in the method of the invention, different types of polymers may be obtained. Indeed, the method according to the invention may lead to a linear polymer or a network polymer depending on the solvation of the compounds of formula (I) defined earlier in the reaction solvent. Therefore, there is a selectivity of the functionality of the compound of formula (I) according to the nature of the polymerization solvent.

Within the scope of the invention, and unless indicated otherwise, by network polymer is meant a cross-linked polymer.

According to an embodiment, the solvent may be selected from solvents allowing solvation of the compound of the aforementioned formula (I), notably DMF, N-methylpyrrolidone (NMP) or DMSO. Preferably, the solvent used is DMF. The use of such solvents may allow solubilization of the compound of formula (I) in said reaction solvent, which implies that all the alcohol functions of the glycolipid monomer borne both by the fatty chain and by the sugar may react. Thus, the method carried out in such a solvent may lead to the preparation of a network polymer, and more particularly to a network polyurethane.

According to another embodiment, the solvent is selected from solvents not allowing solvation of the compound of the aforementioned formula (I), notably THF, diethyl ether or ethyl acetate. Preferably, the solvent used is THF. The use of such solvents does not allow solubilization of the compound of formula (I) in said reaction solvent, which implies that all the alcohol functions of the glycolipid monomer cannot react. Notably, the reaction carried out in a solvent such as THF does not allow solubilization of the alcohol functions borne by the sugar unit of the glycolipid monomer. In such a solvent, said compounds may appear as inverse micelles, in which the sugar portions gather together and are again found inside said micelles, while the fatty chain portions of the compounds (I) are again found on the outside. Thus, only the alcohol functions borne by the fatty chain may react. Indeed, the fatty chain portion is soluble in a solvent such as THF. Although the fatty chain portion of the compound (I) is soluble, the sugar portion of the compound (I) on the other hand proves to be insoluble. Consequently, the reaction solvent does not globally allow solvation of the compound (I).

Thus, the method of the invention carried out in such a solvent may lead to the preparation of a linear polymer, and more particularly to a linear polyurethane, in which the sugar units are pendant.

According to the invention, the ratio between the isocyanate functions and the alcohol functions of the glycolipid monomer used in the method of the invention may also play a role on the nature of the polymer obtained according to the method. Indeed, it is possible to obtain a vast range of polyurethanes ranging from linear oligomers with low molecular masses to network polymers, but it is also possible to obtain branched polymers. Thus, there exists a vast possible range of branched polymers, having a higher or lower branching degree, depending on the ratio between the isocyanate functions and the alcohol functions of the glycolipid monomer used during the polymerization reaction. Typically, in a solvent not allowing solvation of the aforementioned compound (I) such as THF, the more said ratio increases, i.e. the more (poly)isocyanate compound is introduced, the more the number of hydroxyl functions of the fatty chain portion of the glycolipid monomer which may react, increases, thus leading to a linear polymer. Once all the hydroxyl functions of the fatty chain portion have reacted, more the ratio increases and the more certain hydroxyl functions of the sugar portion will be able to react. This thus results in the formation of branches and therefore in the obtaining of a branched polymer. Consequently, the more the ratio between the isocyanate functions and the hydroxyl functions increases and the more the tendency will be towards an increasingly branched polymer.

Within the scope of the invention, and unless indicated otherwise, by <<branched polymer>>, is meant a polymer comprising from one to more branches, but without being cross-linked. Such a polymer is different from a network polymer.

According to another aspect, the method according to the invention may comprise a step for reacting a compound of formula (I) as defined above, with:
a diol from the group consisting of alkane-diols, polyalkylene-diols and diols having one of the formulae (II) or (Ill) as defined above;
a diisocyanate of formula (O)CN-A$_3$-NC(O) wherein A$_3$ is as defined above,
at a temperature comprised from 40° C. to 100° C., preferably at 60° C., in a solvent.

According to a particular embodiment, the diol used in the method is a compound of formula (II):

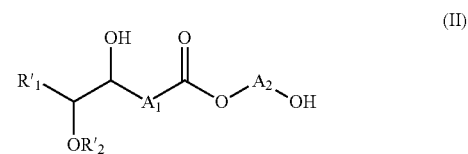

wherein:
R'$_1$ represents a linear or branched alkyl group comprising from 2 to 14 carbon atoms;
R'$_2$ represents a linear or branched alkyl group, comprising from 1 to 8 carbon atoms;
A$_1$ represents a linear or branched, divalent alkylene radical, comprising from 2 to 14 carbon atoms;
A$_2$ represents a linear or branched divalent alkylene radical, comprising from 1 to 10 carbon atoms.

Preferentially, the diol used in the method is a compound of formula (II) in which R'$_1$ represents an octyl group, R'$_2$ represents an ethyl group, A$_1$ represents a heptylene radical and A'$_2$ represents a pentylene radical.

According to a particular embodiment, the diol used in the method is a compound of formula (III):

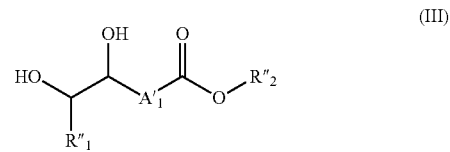

Preferentially, the diol used in the method is a compound of formula (III) in which R"$_1$ represents an octyl group, R"$_2$ represents an ethyl group and A'$_1$ represents a heptylene radical.

According to an embodiment, in the method according to the invention, when R' represents a group (B) or (B') as defined earlier, the diol used is preferably the diol of formula (III).

According to an embodiment, in the method according to the invention, when R' represents a group (D) or (D') as defined earlier, the diol used is preferably the diol of formula (II).

According to an embodiment, the solvent used in the method may be selected from solvents allowing solvation of the compound of the aforementioned formula (I), notably DMF or DMSO, in order to obtain a network polyurethane.

According to another embodiment, the solvent used in the method may be selected from solvents not allowing solvation of the compound of formula (I), notably THF, in order to obtain a linear polyurethane.

Thus, polymers, and notably polyurethanes which are bio-compatible, were prepared from bio-sourced monomers.

It was shown that there exists a selectivity of the functionality of the glycosylated monomers of the invention, depending on the nature of the solvent used in the method. Such selectivity gives the possibility of leading in a controlled way both to linear polymers but also to network polymers.

Thus, novel polyurethanes having quite unexpected physico-chemical properties for polyurethanes were prepared. Indeed, the polyurethanes according to the invention have improved physico-chemical, thermo-mechanical and flow properties relatively to the polyurethanes derived from derivatives of fat known from the state of the art. The latter generally have limited thermo-mechanical properties, such as a low glassy transition temperature and small moduli.

The inventors have advantageously shown that by incorporating the glycolipid monomers according to the invention it is possible to modulate and improve the thermo-mechanical, physico-chemical and flow properties of the resulting polyurethanes. The polyurethanes according to the invention advantageously have glassy transition temperatures which may be modulated from −40° C. to +150° C.

Thus, by incorporating glycolipid monomers according to the invention it is possible to obtain polyurethanes in the form of much more rigid solids than the polyurethanes derived from fat which are in the form of viscous oils.

According to another aspect of the invention, the obtained polymers may be used for vectorization, encapsulation or molecular recognition, notably in the medical, pharmaceutical or cosmetic fields; chromatographic separation notably in the field of analysis; or for preparing adhesives, co-surfactants or coatings. According to the invention, the use may depend on the nature of the obtained polymer, i.e. whether it is linear, more or less branched, or is a network polymer.

According to another aspect, the invention relates to the intermediate compounds fitting the following formula (I'):

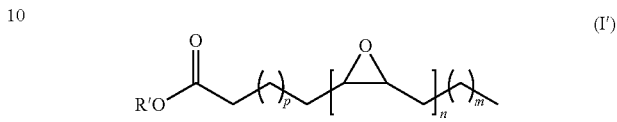

wherein:
R' is selected from sugars or sugar-alcohols;
n is comprised from 1 to 3;
m is comprised from 1 to 6; and
p is comprised from 1 to 9.

According to an embodiment, the intermediate compounds of formula (I') are selected from the following compounds:

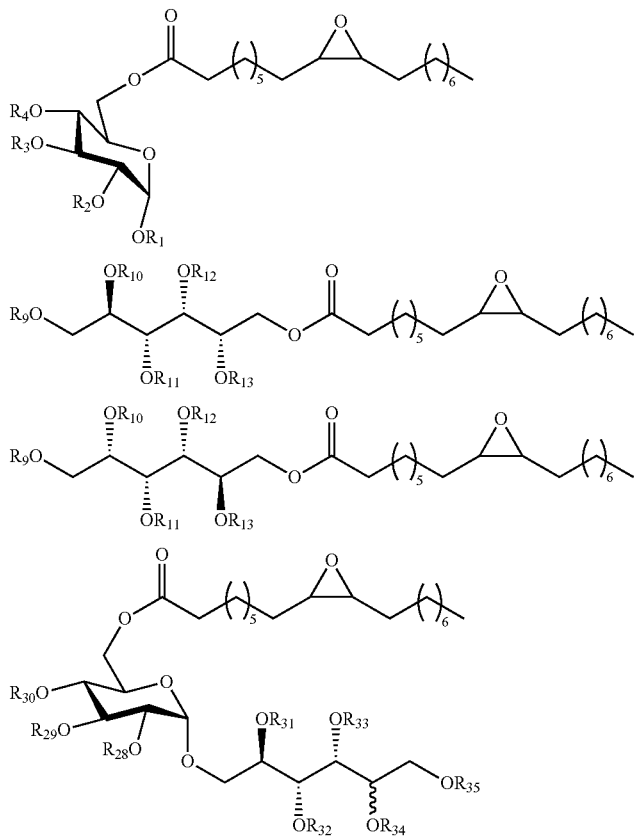

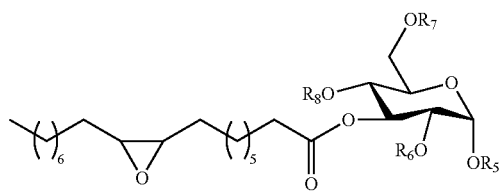

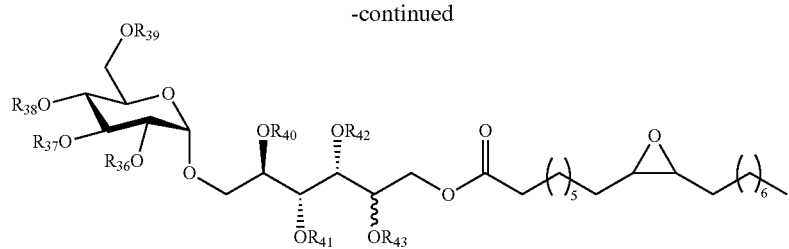
Preferably, the intermediate compounds of the aforementioned formula (I'), are selected from the following compounds:
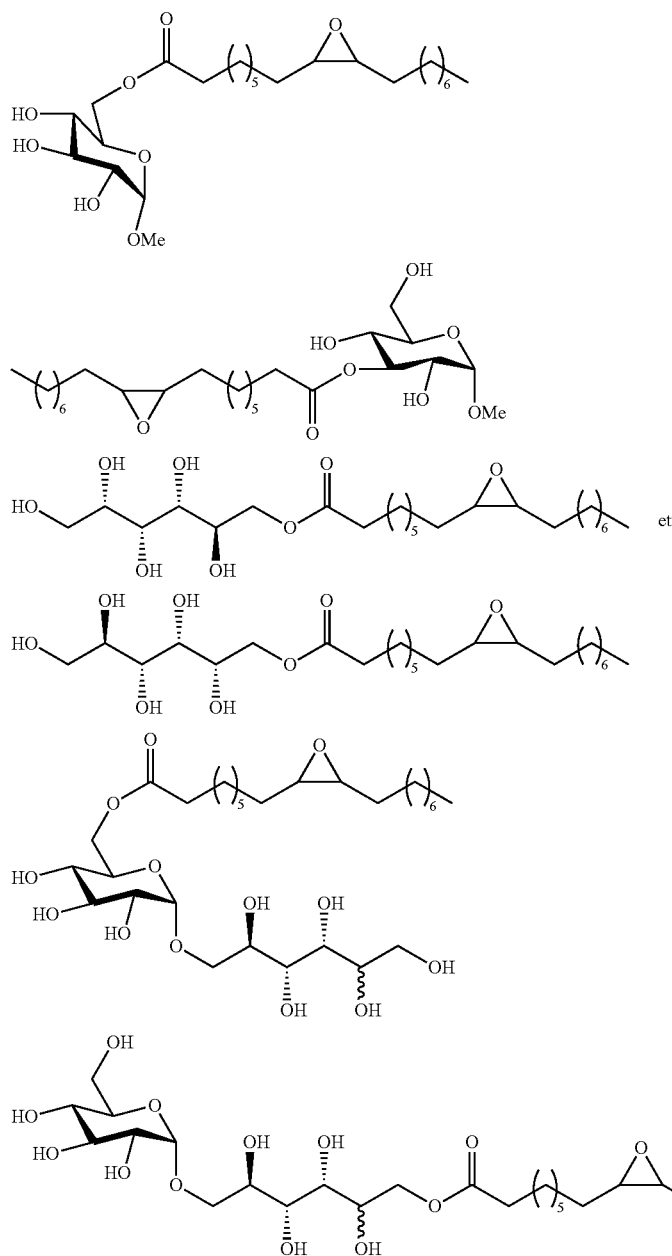

According to the invention, the compounds of formula (I) may be obtained in two steps:

a) transesterification of a compound of the following formula (V):

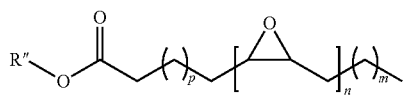

wherein:

R″ represents an alkyl group comprising from 1 to 10 carbon atoms, preferably from 1 to 5 carbon atoms;

n is an integer comprised from 1 to 3;

m is an integer comprised from 1 to 6; and p is an integer comprised from 1 to 9.

with a compound selected from the following sugars or sugar-alcohols:

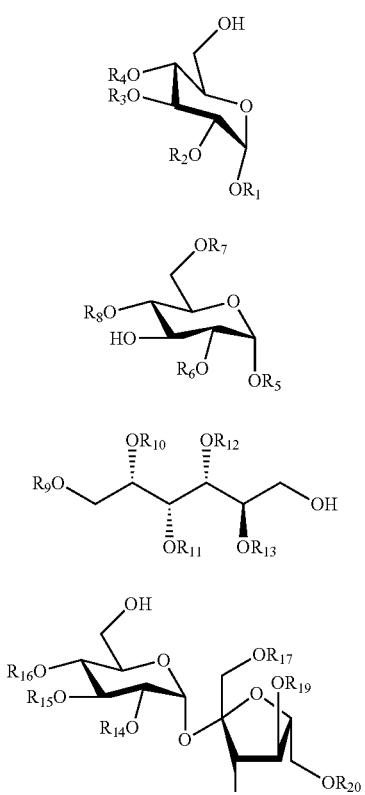

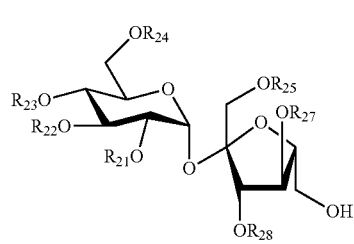

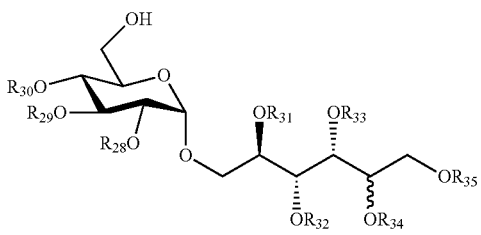

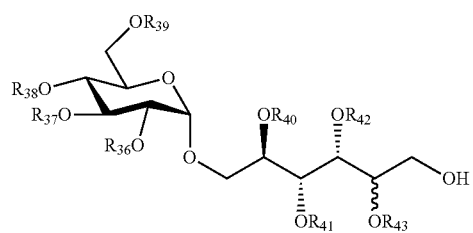

wherein the groups $R_1$ to $R_{43}$ are as defined earlier;

in order to lead to the intermediate compound of formula (I′); and b) a hydrolysis of the epoxide function for leading to the compounds of formula (I) as defined earlier.

Preferably, the preferred compounds of formula V) are those for which n has a value of 1 and R″ represents a methyl or ethyl.

Typically, the transesterification reaction a) may be carried out in any type of solvent, preferably those which cannot react with one of the reagents, in the presence of an acid or basic catalyst. Preferably, the reaction according to the invention is carried out in DMSO in the presence of $K_2CO_3$ as a basic catalyst.

Typically, the reaction a) may be carried out at a temperature comprised from 30° C. to 100° C. Preferably, the reaction a) may be carried out from 50° C. to 95° C. and preferentially from 60° C. to 90° C.

According to an embodiment, the hydrolysis step b) may be carried out in a solvent at a temperature comprised from 30° C. to 100° C. Preferably, the reaction is carried out in dimethylisosorbide (DMI) or in DMSO at a temperature comprised from 50° C. to 90° C., and preferentially from 80° C. to 90° C.

Typically, the hydrolysis may be carried out in the presence of an acid selected from hydrochloric acid, sulfuric acid, nitric acid and phosphoric acid. Preferably, the hydrolysis b) is carried out in the presence of phosphoric acid.

According to another embodiment, the compounds of formula (I) may be obtained in a single step by a transesterification reaction of a compound of the following formula (VI):

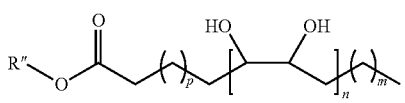

wherein:

R″ represents an alkyl group comprising from 1 to 10 carbon atoms, preferably from 1 to 5 carbon atoms;

n is an integer comprised from 1 to 3;

m is an integer comprised from 1 to 6; and p is an integer comprised from 1 to 9.

with a compound selected from the sugars or sugar-alcohols of formulae (B), (B'), (C), (D), (D'), (E) or (E') as defined earlier, in order to lead to the products of formula (I) as defined earlier.

The following examples allow an illustration of the invention without, however, limiting it.

EXAMPLES

Abbreviations

AcOEt: Ethyl acetate;
AOG: 6-O methyl α-D-glucopyranosyl-9,10-dihydroxy octadecanoate (also called methyl α-D-glucopyranoside 9,10-dihydroxystearate) (compound D);
MeOH: Methanol;
DAM: Dichloromethane/Acetone/Methanol
DMI: Dimethylisosorbide;
CTAB: Hexadecyltrimethylammonium bromide;
IPDI: Isophorone diisocyanate;
DBTDL: Dibutyltin dilaurate.
Suppliers:

| Types | Reagents | Suppliers |
|---|---|---|
| Sugars | α-D-methylglucoside | Sigma-Aldrich |
| | Sorbitol | Sigma-Aldrich |
| | Isomalt | Cargill Deutschland GmbH |
| | Saccharose | Alfa-Aesar |
| Fatty esters | Methyl oleate (99%)° | Aldrich |
| | Ethyl oleate (85%) | ITERG |
| | Epoxidized methyl oleate (85%) | ITERG |
| Acids and Bases | $H_3PO_4$ (85%) | Carlo-Erba |
| | $K_2CO_3$ | Carlo-Erba |
| | $NH_4Cl$ | Carlo-Erba |
| | $NaHCO_3$ | Prolabo |
| | $HCO_2H$ | Prolabo |
| | m-CPBA | Aldrich |
| Solvents | DMSO | Carlo-Erba |
| | DMI | Roquettes |
| | $CH_2Cl_2$ | SDS |
| | Ethyl acetate | SDS |
| | n-Butanol | Sigma-Aldrich |
| | Acetonitrile | SDS |
| | $Na_2SO_4$ | SDS |
| | $H_2O_2$(35%) | Sigma-Aldrich |

A. Synthesis of the Monomers

Example 1

Preparation of 6-O-α-D-methylglucosyl 9,10-dihydroxy-octadecanoate (2)

1) Synthesis of methyl 9,10-epoxy-octadecanoate (B)

To 3.5 g of methyl oleate (11.8 mmol; 1 equiv.) and 0.18 mL of formic acid (4.7 mmol; 0.4 equiv.), at 0° C., were added drop wise 2.1 mL of hydrogen peroxide (35% by weight. aq.; 70.7 mmol; 6 equiv.). The reaction medium was stirred for 4 h at room temperature and then at 40° C. After 16 h, total conversion of the methyl oleate by TLC (Pentane/ethyl acetate 98/2) was observed. After neutralization to pH=7 with a saturated $NaHCO_3$ solution, the mixture was extracted with ethyl acetate (3×25 mL). The organic phases were washed with 75 mL of a saturated NaCl solution, dried on $Na_2SO_4$, filtered and then dry-evaporated. The compound (B) was obtained with a yield of 98% (yellow oil).

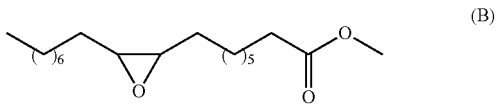

2) Synthesis of 6-O-α-D-methylglucosyl 9,10-epoxy-octadecanoate (1) and of 3-O-α-D-methylglucosyl 9,10-epoxy-octadecanoate (1') by transesterification In a 250 mL flask provided with a magnetised bar and a distillation system, 10 g of epoxidized methyl oleate (32 mmol) (B), 4 equiv. of 1-O-methyl-α-D-glucopyranoside (24 g; 128 mmol) and 0.2 equiv. of $K_2CO_3$ (0.9 g; 6.4 mmol) were dissolved in 70 mL of DMSO, and the reaction medium was left under reduced pressure (14-27 mmHg) from 70° C. to 90° C. The reaction was followed with TLC.

After total conversion of the epoxidized methyl oleate (B), the DMSO was evaporated under reduced pressure. The residue was solubilized in 300 mL of distilled water and extracted with ethyl acetate (3×250 mL). The organic phases were washed with 200 mL of a saturated NaCl solution. The organic phase was dried on $Na_2SO_4$, filtered and the ethyl acetate was evaporated under reduced pressure. The crude was purified by chromatography on normal silica with a pentane/AcOEt gradient ranging from 60/40 to 2/98 in order to obtain 11 g of a mixture of methylglucoside (1) and (1') monoesters (73%).

The $C_6$ monoester of the methylglucoside (1) was able to be isolated by precipitation in a cold pentane/AcOEt:80/20 mixture. 5.4 g of a white powder may be obtained after filtration on a frit (yield of 36%).

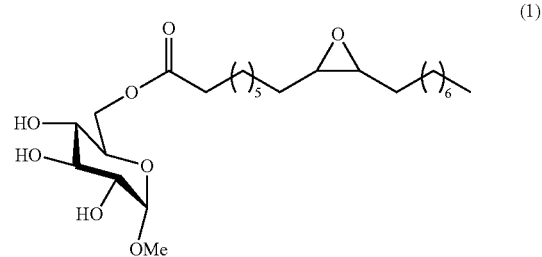

Rf: 0.34 (AcOEt/pentane:9/1)

$^1$H NMR (CDCl$_3$, 400 MHz): 4.73 (d; 1H; =4.4 Hz; H-1); 4.34-4.40 (dd; 1H, $J_{5-6a}$=6.7 Hz; $J_{6a-6b}$=15.2 Hz; H-6a); 4.26-4.33 (dd; 1H; $J_{5-6b}$=6.7 Hz; $J_{6a-6b}$=15.2 Hz; H-6b); 3.67-3.77 (m; 2H; H-3 and H-5); 3.51 (m; H; H-2); 3.40 (s; 3H; OCH$_3$ (methylglucopyranoside)); 3.32 (t; 1H; J=12.6 Hz; H-4); 2.88 (m; 2H; H-9' and H-10'); 2.35 (t; 2H; J=10.4 Hz; CH$_2$ (α OCO)); 1.15-1.70 (m; 26H; CH$_2$ (alkyl chain)); 0.86 (t; 3H; J=8.8 Hz; CH$_3$)

$^{13}$C NMR (CDCl$_3$, 100 MHz): 175.5 (C=O); 99.8 (C-1); 74.5 (C-3); 72.4 (C-2); 70.6 (C-4); 70.1 (C-5); 63.8 (C-6); 57.4 (C-9' et 0-10'); 55.4 (OCH$_3$ (methylglucopyranoside); 34.5 (CH$_2$ (α OCO)); 23.1-34.6 (CH$_2$ (alkyl chain)); 14.5 (CH$_3$)

MS: (high resolution) m/z [M+Na]$^+$ calculated mass=497.3085
measured mass=497.3066

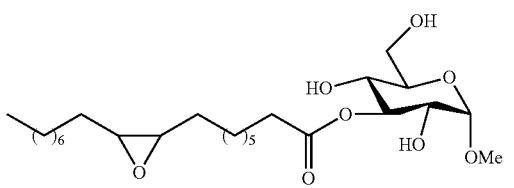

(1')

Rf: 0.55 (AcOEt/pentane:9/1)

$^1$H NMR (CDCl$_3$, 400 MHz): 5.05 (t; 1H; $J_{3-4}=J_{2-3}$ 9.2 Hz; H-3); 4.70 (d; 1H; $J_{1-2}$=3.7 Hz; H-1); 3.80-3.92 (m; 2H; H-6a,b); 3.55-3.70 (m; 3H; H-2; H-4 et H-5); 3.40 (s; 3H; OCH$_3$ (methylglucopyranoside)); 2.90 (m; 2H; H-9' et H-10'); 2.41 (t; 2H; J=10.4 Hz; CH$_2$ ($\alpha$ OCO)); 1.20-1.75 (m; 26H; CH$_2$ (alkyl chain)); 0.87 (t; 3H; J=8.8 Hz; CH$_3$)

$^{13}$C NMR (CDCl$_3$, 100 MHz): 176.0 (C=O); 99.7 (C-1); 77.6 (C-3); 71.8 (C-5); 71.1 (C-2); 69.6 (C-4); 62.6 (C-6); 57.7 (C-9' et C-10'); 55.8 (OCH$_3$ (methylglucopyranoside); 34.5 (CH$_2$ ($\alpha$ OCO)); 23.06-32.2 (CH$_2$ (alkyl chain)); 14.5 (CH$_3$).

MS: (high resolution) m/z [M+Na]$^+$ calculated mass=497.3085
measured mass=497.3066

3) Synthesis of 6-O-α-D-methylglucosyl 9,10-dihydroxy-octadecanoate (2)

In a 50 mL flask provided with a magnetized bar, 1 g of epoxidized methylglucoside (1) oleate monoester (2.1 mmol) were dissolved in 1.8 mL of dimethylisosorbide (DMI) at 50° C., and then 5.6 mL of a solution of H$_3$PO$_4$ (5% by mass in water) were slowly added and the reaction medium was brought to 80° C. The reaction was followed with TLC. After 3-4-h of reaction, there was conversion of (1) (with TLC). The reaction medium was extracted with ethyl acetate (2×50 mL) and the organic phases were washed with a saturated NaHCO$_3$ solution to a pH equal to 7 and then with a saturated NaCl solution (75 mL). The organic phases were dried on Na$_2$SO$_4$, filtered and the ethyl acetate evaporated under reduced pressure. 15 mL of ether were added to the residue at 0° C. A solid precipitated, and then was filtered in order to recover the methylglucoside diol oleate monoester (2) (0.64 g; yield 62%).

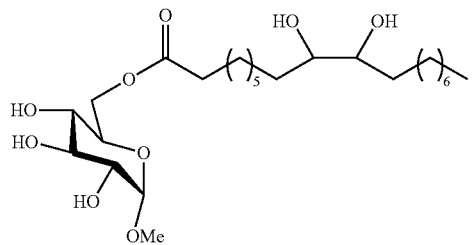

(2)

Rf: 0.41 (DAM: Dichloromethane/Acetone/Methanol:8/1/1)

$^1$H NMR (CD$_3$OD, 400 MHz): 4.73 (d; 1H; $J_{1-2}$=4.4 Hz; H-1); 4.34-4.40 (dd; 1H, $J_{5-6a}$=6.7 Hz; $J_{6a-6b}$=15.2 Hz; H-6a); 4.26-4.33 (dd; 1H; $J_{5-6b}$=6.7 Hz; $J_{6a-6b}$=15.2 Hz; H-6b); 3.67-3.77 (m; 2H; H-3 and H-5); 3.64-3.71 (m; 2H; H-9' and H-10'); 3.51 (m; 2H; H-2); 3.40 (s; 3H; OCH$_3$ (methylglucopyranoside)); 3.32 (t; 1H; J=12.6 Hz; H-4); 2.35 (t; 2H; J=10.4 Hz; CH$_2$ (a 000)); 1.15-1.70 (m; 26H; CH$_2$ (alkyl chain)); 0.86 (t; 3H; J=8.8 Hz; CH$_3$).

$^{13}$C NMR (CD$_3$OD, 100 MHz): 175.5 (C=O); 101.6 (C-1); 75.6 (C-9' et C-10'); 75.4 (C-3); 73.8 (C-2); 72.2 (C-4); 71.4 (C-5); 65.1 (C-6); 56.04 (OCH$_3$ (methylglucopyranoside); 35.5 (CH$_2$ ($\alpha$ OCO)); 24.5-34.4 (CH$_2$ (alkyl chain)); 14.9 (CH$_3$).

MS: (high resolution) m/z [M+Na]$^+$ calculated mass=515.3191
measured mass=515.3181

Example 2

Preparation of 1-O-D-sorbitol 9,10-dihydroxy-octadecanoate (4) and of 6-O-D sorbitol 9,10-dihydroxy-octadecanoate (4')

1) Synthesis of sorbitol esters: 1-O-D-sorbitol 9,10-epoxy-octadecanoate (3) and 6-O-D-sorbitol 9,10-epoxy-octadecanoate (3'), by transesterification In a 100 mL flask provided with a magnetized bar and a distillation system, 5 g of epoxidized methyl oleate (B) (16 mmol), 4 equiv. of D-sorbitol (11.7 g; 64 mmol) and 0.2 equiv. of K$_2$CO$_3$ (0.4 g; 3.2 mmol) were dissolved in 35 mL of DMSO, and the reaction medium was left under reduced pressure (14-27 mmHg) from 70° C. to 90° C. The reaction was followed with TLC. After total conversion of the epoxidized methyl oleate (B), the DMSO was evaporated under reduced pressure. The residue was solubilized in 150 mL of distilled water and extracted with ethyl acetate (3×150 mL) and the organic phases were washed with 200 mL of a saturated NaCl solution. The organic phases were dried on Na$_2$SO$_4$, filtered and ethyl acetate was evaporated under reduced pressure. The crude was purified by chromatography on normal silica with a pentane/AcOEt gradient ranging from 60/40 to 2/98 in order to obtain 7.2 g of a mixture of sorbitol monoesters (3) and (3') with the aspect of a partially solid gel. The monoesters may be purified by precipitation from cold methanol. 5.2 g of brown solid after filtration on a frit and washing with pentane may be obtained (yield 70%).

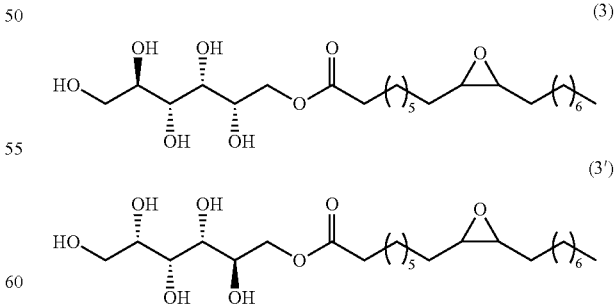

(3)

(3')

Rf 0.37 (AcOEt/MeOH 95/5)

$^1$H NMR (CD$_3$OD, 400 MHz): δ(ppm) 4.37 (dd, 1H, J 15.2 Hz. J 3.5 Hz. COOCH$_2$ A), 4.24 (dd, 1H, J 15.2 Hz, J 1.5 Hz, COOCH$_2$ B), 4.18 (dd, 1H, J 15.2 Hz, J 6.1 Hz, COOCH$_2$ B), 4.16 (dd, 1H, J 15.2 Hz. J 3.5 Hz. COOCH$_2$ A), 4.01-3.85 (m, 4H, C$\underline{H}$OH sorbitol), 3.82-3.59 (m, 8H, C$\underline{H_2}$OH A and B and C$\underline{H}$OH sorbitol), 2.95 (m, 4H, H-9' and H-10'), 2.39 (2t, 4H, J=10.04 Hz, CH$_2$CO), 1.31-1.65 (m, 52H, CH$_2$), 0.95 (t, 6H, J=8.8 Hz, CH$_3$).

$^{13}$C NMR (CD$_3$OD, 125 MHz): δ(ppm) 175.8 and 175.5 (2×C=O), 75.1, 73.7, 73.5, 73.3, 73.0, 72.6, 70.9, 70.5 (2), 67.4 (COOC$\underline{H_2}$ A), 66.7 (COOC$\underline{H_2}$ B), 64.8 (CH$_2$OH A or B), 64.1 (C$\underline{H_2}$OH A or B), 58.7 (2×C-9 and C-10 epoxides), 55.7 (2×OCH$_3$), 35.0 (2×CH$_2$CO), 23.7-33.0 (CH$_2$ alkyl chain), 14.4 (2×CH$_3$).

MS: (high resolution) m/z [M+Na]$^+$ calculated mass=485.3085 measured mass=485.3063

2) Preparation of 1-O-D-sorbitol 9,10-dihydroxy-octadecanoate (4) and of 6-O-D-sorbitol 9,10-dihydroxy-octadecanoate (4')

a) Use of DMI as a Co-Solvent

In a 100 mL flask provided with a magnetised bar, 3.1 g of the epoxidized sorbitol oleate (3) and (3') mixture (6.7 mmol) were dissolved in 4.1 mL of dimethyl isosorbide at 50° C., and then 11.5 mL of a solution of H$_3$PO$_4$ (5% by mass in the water) were slowly added. The reaction medium was brought to 80-90° C. and the reaction was followed with TLC. After 5 h of reaction, there was conversion of the epoxides (3) and (3') (with TLC) and the reaction medium was cooled to room temperature. A yellow gel precipitated, and was then filtered and washed with ethyl ether in order to obtain a yellow solid. This solid was dissolved in 150 mL of ethyl acetate and then washed 4 times with distilled water and with a saturated NaHCO$_3$ solution, and then with a saturated NaCl solution. The organic phase was dried on Na$_2$SO$_4$, filtered and the solvent was evaporated under reduced pressure. 2.3 g of a mixture of diols (4) and (4') (74%) contaminated with residual DMI were obtained.

b) Use of DMSO as a Co-Solvent

In a 100 mL flask provided with a magnetized bar, 2 g of the mixture of epoxides (3) and (3') (4.1 mmol) were dissolved in 4.1 mL of DMSO at 50° C., and then 11.5 mL of a solution of H$_3$PO$_4$ (5% by mass in the water) were slowly added. The reaction medium was brought to 80-90° C. and the reaction was followed with TLC. After 5 h of reaction, there was disappearance of the epoxide (3)/(3') (with TLC) and the reaction medium was left to cool down to room temperature. A white gel precipitated, was filtered and dissolved in 150 mL of ethyl acetate and was then washed 4 times with distilled water and with a saturated NaHCO$_3$ solution, and then with a saturated NaCl solution. The organic phase was dried on Na$_2$SO$_4$, filtered and then concentrated under reduced pressure. Purification by cold precipitation from diethyl ether gave the possibility of obtaining 1.8 g of a mixture of diols (4) and (4') (82%).

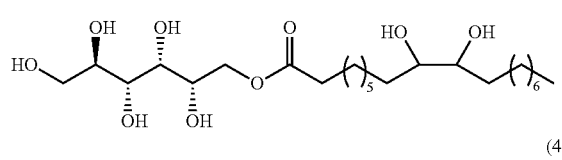
(4)

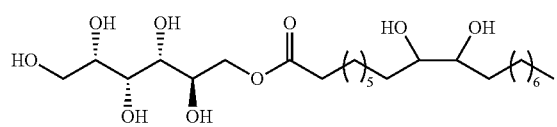
(4')

Rf: 0.44 (AcOEt/MeOH:9/1)

$^1$H NMR (CD$_3$OD, 323K, 400 MHz) δ(ppm) 4.66 (dd, 1H, J=11.6 Hz, J 2.8 Hz, COOC$\underline{H_2}$ A), 4.54-4.46 (m, 2H, COOC$\underline{H_2}$ B), 4.46 (dd, 1H, J 11.7 Hz, J 6.2 Hz, COOCH$_2$ A), 4.28-4.12 (m, 4H, C$\underline{H}$OH sorbitol), 4.10-3.89 (m, 8H, C$\underline{H_2}$OH A and B and C$\underline{H}$OH sorbitol and C$\underline{H}$OH sorbitol), 3.67 (m, 4H, H-9' and H-10' dihydroxy), 2.66 and 2.65 (2t, 4H, J 7.5 Hz, 2×CH$_2$CO), 1.60-1.90 (m, 2×26H, CH$_2$), 1.19 (t, 6H, J 6.3 Hz, CH$_3$).

$^{13}$C NMR (CD$_3$OD, 323K, 100 MHz) δ(ppm) 175.8 and 175.6 (2×C=O), 75.4 and 75.3 (C$\underline{H}$OH 9,10-dihydroxy), 75.0, 73.8, 73.5, 73.2, 72.6, 71.1, 70.9 (2), 67.4 (COOC$\underline{H_2}$ A), 66.7 (COOC$\underline{H_2}$ B), 64.9 (CH$_2$OH A or B), 64.3 (C$\underline{H_2}$OH A or B), 35.1 and 35.0 (C$\underline{H_2}$CO), 34.1-23.6 (aliphatic CH$_2$), 14.3 (CH$_3$).

MS: (high resolution) m/z [M+Na]$^+$ calculated mass=503.3191 measured mass=503.3188

Example 3

Preparation of Saccharose Esters: 6-O-saccharose 9,10-dihydroxy-octadecanoate (6) and (6')

1) Synthesis of methyl 9,10-dihydroxy-octadecanoate (C)

In a 100 mL flask, provided with a magnetized bar, 1 g of epoxidized methyl oleate (B) (3.1 mmol) were dissolved in 5.8 mL of dimethyl isosorbide (DMI), and then 8 mL of a solution of H$_3$PO$_4$ (5% by mass in the water) and 0.1 g of hexadecyltrimethylammonium bromide (CTAB) (0.31 mmol; 0.1 equiv.) were added dropwise. Next, the reaction medium was brought to 80-90° C. After conversion of the epoxidized methyl oleate (with TLC), the mixture is cooled down to room temperature for 14 h. A precipitate was filtered on a frit. The solid was solubilized in 100 mL of ethyl acetate and washed with distilled water (6×100 mL) and with a saturated NaHCO$_3$ solution to a pH of about 7 and then with a saturated NaCl solution (twice 50 mL). The solution was dried on Na$_2$SO$_4$, filtered and evaporated. The compound (C) was obtained with a yield of 86% (yellowish solid containing residual DMI).

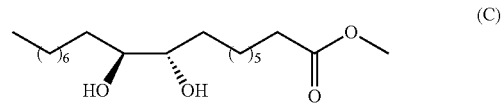
(C)

Rf: 0.27 (Ethyl acetate/pentane: 2/8)

$^1$H NMR (CDCl$_3$, 300 MHz): 3.62 (s; 3H; OCH$_3$); 3.36-3.40 (m; 2H; H-9 and H-10); 2.26 (t; 2H; J=7.5; CH$_2$ (α OCO)); 1.23-1.61 (m; 26H; CH$_2$ (alkyl chain)); 0.84 (t; 3H; J=6.9; CH$_3$).

$^{13}$C NMR (CDCl$_3$, 75 MHz): 174.2 (C=O); 75.3 (C-9; C-10); 51.7 (C—OCH$_3$); 34.1 (CH$_2$ (α OCO)); 22.7-31.9 (CH$_2$ (alkyl chain)); 14.1 (CH$_3$).

MS: (high resolution) m/z [M+Na]$^+$ calculated mass=353.2662 measured mass=353.2657

2) Synthesis of 6 or 6'-O-saccharose 9,10-dihydroxy-octadecanoate (6) and (6') by transesterification In a 500 mL flask provided with a magnetized bar and a distillation system, 18 g of methyl dihydroxy-oleate (C)

(83% by weight; 43.5 mmol), 4 equiv. of saccharose (50.6 g; 147 mmol) and 0.2 equiv. of K$_2$CO$_3$ (1.02 g; 7.4 mmol) were dissolved in 130 mL of DMSO, and the reaction medium was stirred under reduced pressure (14-27 mmHg) from 70° C. to 90° C. After total conversion of the diol (C) (TLC), the DMSO was evaporated under reduced pressure. The residue was solubilised in 250 mL of distilled water and first extracted with ethyl acetate (100 mL) and then with butanol (3×150 mL) and the organic phases were washed with 200 mL of saturated NaCl solution. The organic phases were dried on Na$_2$SO$_4$, filtered and the butanol was evaporated under reduced pressure (co-evaporated with methanol in order to remove the trace amounts of butanol). 6.3 g of the crude mixture (6) and (6') were purified by chromatography on a column with an elution gradient from DAME-A to DAME-C in order to obtain 3.4 g of saccharose monoesters including (6) and (6').

(30.6 mmol), 4 equiv. of isomalt (44 g; 128 mmol) and 0.2 equiv. of K$_2$CO$_3$ (0.8 g; 6.4 mmol) were dissolved in 110 mL of DMSO. The reaction medium was stirred under reduced pressure (14-27 mmHg) from 70° C. to 90° C. The reaction was followed with TLC. After total conversion of the epoxidized methyl oleate (B), the DMSO was evaporated under reduced pressure. The residue was solubilized in 250 mL of distilled water and extracted with butanol (3×150 mL) and the organic phases were washed with 200 mL of saturated NaCl solution. The organic phases were dried on Na$_2$SO$_4$, filtered, and the butanol was evaporated under reduced pressure. 9 g of crude were purified by chromatography on a column with an elution gradient of Dichloromethane/Acetone/Methanol/Water:78/10/10/2 to 56/20/20/4 in order to obtain 5.2 g of a mixture containing the isomalt monoesters (7) and (7').

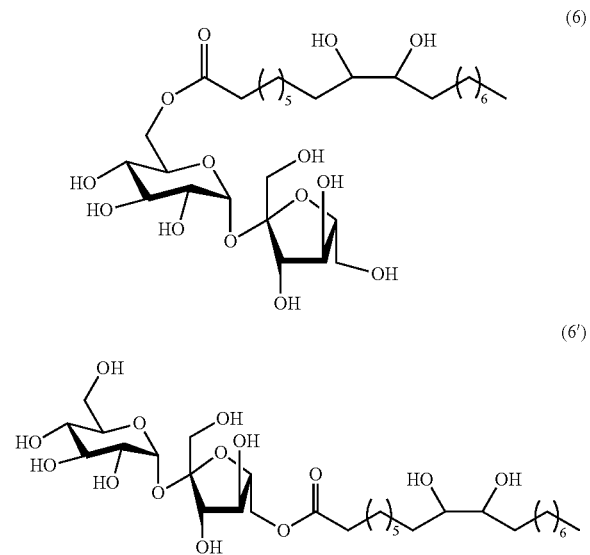

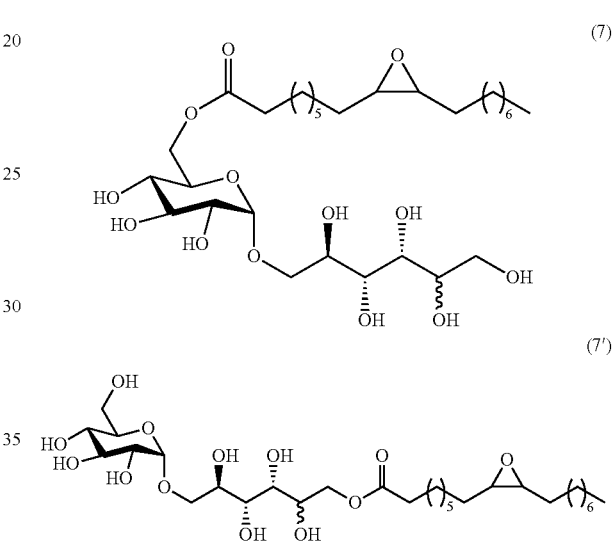

Rf: 0.30 (DAME-C)

The NMR analysis of the mixture after chromatography is as follows:

$^1$H NMR (CD$_3$OD; 400 MHz) (main signals): 5.36 (m, 2H, H-1 sucrose), 4.43-4.40 (m, 3H, C$\underline{H}_2$OCO), 4.11-3.33 (m, H sucrose and 4H dihydroxy), 2.39 (t, 4H, J 10 Hz, C$\underline{H}_2$CO), 1.75-1.25 (m, 2×26H, CH$_2$), 0.92 (t, 6H, J=8.8 Hz, CH$_3$).

$^{13}$C NMR (CD$_3$OD, 100 MHz) (signaux principaux): 175.5 (C=O), 105.5, 105.2, 104.0 (C-2' sucrose), 93.5 and 93.4 (C-1 sucrose), 83.9-71.5 (CHOH sucrose and CHOH dihydroxy), 66.9 and 64.7 (2×$\underline{C}$H$_2$OCO), 64.1, 63.9, 63.8, 63.2, 62.5 (4×OCH$_2$), 35.1 and 34.9 (2×CH$_2$CO), 35.1-23.7 (CH$_2$ aliphatic), 14.4 (CH$_3$).

MS: (high resolution) m/z [M+Na]$^+$ calculated mass=663.3562 measured mass=663.3560

Example 4

Preparation of Isomalt Esters (8) and (8')

1) Synthesis of 6-O-isomalt 9,10-epoxy-octadecanoate (7) and 6'-O-isomalt 9,10-epoxy-octadecanoate (7') by transesterification In a 500 mL flask provided with a magnetized bar and a distillation system, 10 g of epoxidized methyl oleate (B)

Rf: 0.28 (Dichloromethane/Acetone/Methanol/Water:56/20/20/4)

NMR analysis does not allow clear identification of the obtained products.

MS: (high resolution) m/z [M+Na]$^+$ calculated mass=647.3613 measured mass=647.3612

2) Synthesis of 6-O-isomalt 9,10-dihydroxy-octadecanoate (8) and 6'-O-isomalt 9,10-dihydroxy-octadecanoate (8') by hydrolysis In a 50 mL flask provided with a magnetized bar, 1 g of the epoxidized isomalt oleate (7) and (7') mixture (1.6 mmol) was dissolved in 3 mL of a solution of H$_3$PO$_4$ (5% by mass in the water) at 50° C. Next, the reaction medium was brought to 80-90° C. The reaction was followed with TLC. After 3-4-h of reaction, there is disappearance of the isomalt ester epoxide (7) (with TLC). After having let the medium return to room temperature, a gel precipitated. The latter was recovered by filtration. The gel was solubilized in 50 mL of butanol, and then washed with a saturated NaHCO$_3$ solution to a pH of 7 and then with a saturated NaCl solution (twice 30 mL). The organic phases were dried on Na$_2$SO$_4$, filtered and the butanol was evaporated under reduced pressure (co-evaporated with methanol in order to remove the trace amounts of butanol), in order to obtain 0.9 g of a mixture containing the isomalt oleate diol (8) and (8') monoesters with the aspect of a beige solid.

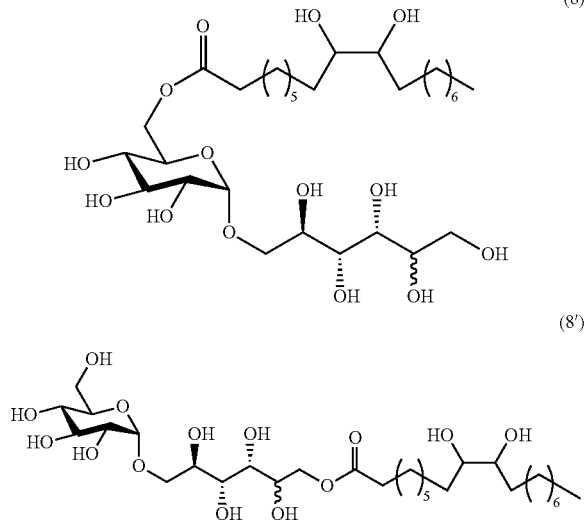

Rf: 0.17 (DAME-C: Dichloromethane/Acetone/Methanol/Water:56/20/20/4)

NMR analysis does not allow clear identification of the obtained products.

MS: (high resolution) m/z [M+Na]$^+$ calculated mass=665.3719 measured mass=665.3697

B. Synthesis of Linear Polyurethanes from the Monomers

The applied procedure described hereafter may be applied to any glycosylated polyol and to any isocyanate.

Example 5

Synthesis of a homopolymer from 6-O methyl α-D-glucopyranosyl-9,10-dihydroxy octadecanoate (also called methyl α-D-glucopyranoside 9,10-dihydroxystearate) (D) or (AOG)

1) Synthesis

The compound (D) was tested as a polyol in the synthesis of novel polyurethanes, in the presence of IPDI.

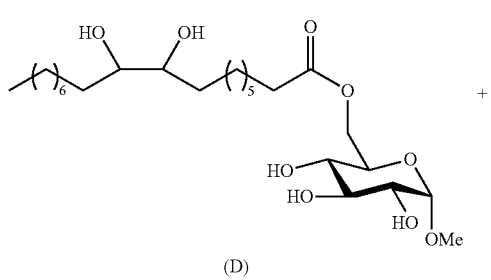

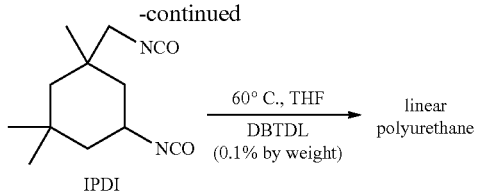

In a 250 mL flask surmounted with a condenser and provided with a magnetized bar were mixed the compound (D) (5 g; 10.1 mmol) dissolved beforehand in 50 mL of THF, IPDI (isophorone diisocyanate) (2.47 g; 11.1 mmol) and the DBTDL (dibutyltin dilaurate) catalyst (7.5 mg sampled with a micropipette). The flask was then immersed in an oil bath heated to 60° C. The conversion of the IPDI was followed by infrared spectroscopy, by the disappearance of the vibration band of the isocyanate functions localized at 2,250 cm$^{-1}$ as well as by the appearance of those of the urethane functions localized at 1,530 cm$^{-1}$. After 20 h, the polyurethane was obtained.

The following table 1 gathers the results of the polymerizations carried out in THF, for different molar isocyanate functions/alcohol functions ratios.

TABLE 1

Experimental results of the polymerizations carried out from the compound (D) and from IPDI in THF.

| | Molar ratio $n_{NCO}/n_{OH}$ | Duration of the reaction $^a$ | NCO conversion | Polymer solubility THF $^b$ | in $M_w$ (g/mol)/IP $^c$ | Tg (° C.) $^d$ |
|---|---|---|---|---|---|---|
| 1 | 1 | 20 h | Incomplete | Insoluble | — | — |
| 2 | 0.7 | 20 h | Incomplete | Insoluble | — | — |
| 3 | 0.5 | 20 h | Incomplete | Insoluble | — | — |
| 4 | 0.38 | 20 h | Total | Soluble | 13,500/1.7 | 39 |
| 5 | 0.2 | 20 h | Total | Soluble | 8,500/1.5 | 38 |

$^a$ Determined when the vibration band of the isocyanate functions at 2,250 cm$^{-1}$ no longer changes.
$^b$ Solubility of the polymer in the solvent when the reaction no longer changes.
$^c$ Determined by SEC chromatography, DMF solvent, PS calibration, IP = dispersity = $M_w/M_n$.
$^d$ DSC, a ramp from −100° C. to 150° C., at 10° C./min.

For molar ratios (isocyanate functions/alcohol functions) comprised between 0.5 and 1 (entries 1, 2 and 3), the conversion of the isocyanate functions remains incomplete, which is expressed by an absence of reactivity of certain alcohol functions.

For molar ratios less than or equal to 0.38, the conversion of the isocyanate functions is complete after 20 h. Remarkably, the thereby obtained polyurethanes are soluble in THF (entries 4 and 5). These results have shown that this threshold value 0.38 corresponds to only considering the sole contribution of only two alcohol functions out of the five which the polyol (D) includes.

Analysis of the $^1$H NMR spectrum of the obtained polyurethane reveals the disappearance of the signal at 4.40 ppm of the two protons of the carbons bearing the alcohol functions of the C$_{18}$ chain. Conversely, the signals localised at 4.25 ppm, 4.50 ppm and 4.75 ppm relating to the protons of the carbons bearing the alcohol functions of the glycoside group have not disappeared, which indicates that these alcohol functions did not react during the polymerization.

The comparison with the $^{13}$C NMR spectrum of the compound (D) shows that the alcohol functions of the C$_{18}$ chain were consumed while those of the glycoside group were retained. Indeed, the signal at 73.17 ppm relating to the two carbons bearing the alcohols of the $C_{18}$ chain disappears at the end of the polymerization, while the peaks at 73.08 ppm, 71.77 ppm and 69.55 ppm corresponding to the carbons of the glycoside group are still present.

The fact that both alcohol functions of the $C_{15}$ chain have reacted with priority in THF is explained by the fact that the glucose is not soluble in THF, unlike the fatty acid derivatives. The selectivity of both of these alcohol function types in this solvent therefore gives the possibility of obtaining linear polyurethanes for a molar ratio close to 0.4.

During the use of an isocyanate function/alcohol function ratio of 0.2, it is noticed that a linear polyurethane was also obtained after total conversion. On the other hand, the obtained molecular mass is smaller. This is explained by the fact that the totality of the hydroxyl functions of the fatty chain portion of the polyol (D) did not react.

On the other hand, upon increasing the ratio from 0.4 to 0.5, the result of this is that all the functions of the fatty chain reacted and that certain hydroxyl functions of the sugar portion may react. The result of this is the formation of branches and therefore the obtaining of a branched polymer. The more the ratio increases and more the tendency will be towards a network polymer.

2) Thermomechanical Properties of the Polyurethanes

The characterization of the polyurethanes by differential enthalpy analysis reveals glassy transition temperatures ($T_g$) close to 38° C. for linear polyurethanes.

Example 6

Synthesis of a Homopolymer from the Oleate Derived from Saccharose

The saccharose ester (E) was tested as a polyol in the synthesis of novel polyurethanes, in the presence of IPDI.

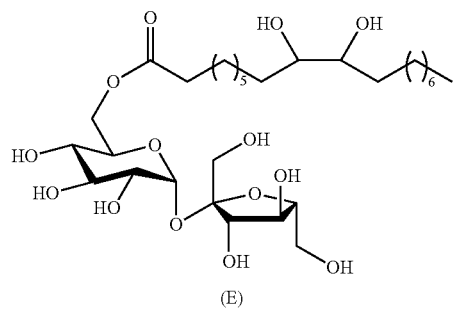

(E)

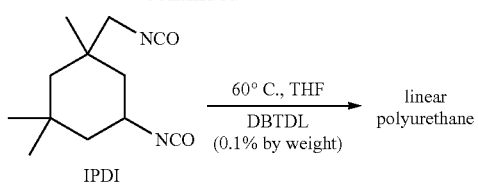

The polymerization was carried out according to the procedure described in example 5.

The following Table 2 gathers the results of the polymerizations carried out in THF, for different isocyanate functions/alcohol functions molar ratios (total duration: 22 h).

TABLE 2

Experimental results of the polymerizations carried out from saccharose and IPDI in THF.

| | (D) ($10^{-4}$ moles) | IPDI ($10^{-4}$ moles) | Molar ratio $n_{NCO}/n_{OH}$ | DBTDL (in μL) | NCO conversion | $M_n$ (g/mol)/IP $T_g$ (in ° C.) |
|---|---|---|---|---|---|---|
| 1 | 7.5 | 7.5 | 1 | 0.66 | Total | 21000-31200 32.6 and 110.9/2-2.25 |
| | 7.5 | 3 | 0.4 | 0.56 | Total | 9900/1.2 18.8 and 69.8 3600/1 |

The polyurethane is obtained as a powder in every case.

Example 7

Synthesis of Compound (D)/HPO (Hydroxylated Pentanol Oleate) Copolymers

1) Synthesis

A series of copolymers were synthesized from hydroxylated pentanol oleate (F), from the compound (D) and in the presence of IPDI.

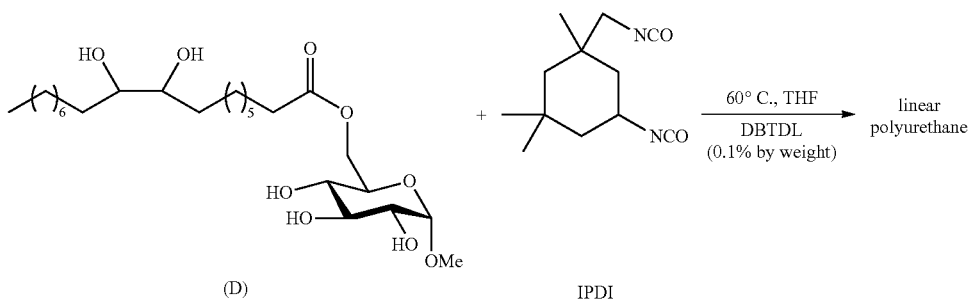

(D)    IPDI

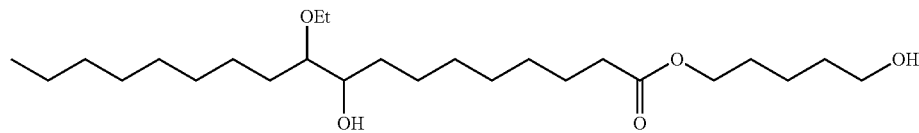

(F)

The polymerization reactions were carried out in THF. Only the two alcohol functions of the $C_{18}$ chain of the compound (D) and the two alcohol functions of HPO were considered for calculating the amount of IPDI to be added. The compound (D) was incorporated to different molar fractions varying from 0 to 100%. The total conversions were attained when the vibration band of the isocyanate functions had completely disappeared in the infrared.

By considering that the molar fraction of AOG (compound (D)), incorporated into the mixture of AOG/HPO monomers is $x_{AOG}$ and that the total mass of diol is 5 g, while the mass of IPDI to be introduced was calculated in the following way:

$$n_{IPDI} = x_{AOG} \cdot n_{AOG} + [(1-x)_{AOG}] \cdot n_{OPH} \quad (1)$$

$$m_{AOG} + M_{OPH} = 5 \quad (2)$$

$(1) + (2) \rightarrow m_{IPDI} =$ $$\left[ M_{IPDI}[x]_{AOG} \cdot \frac{m_{AOG}}{M_{AOG}} + [(1-x)_{AOG}] \cdot \frac{(5-m_{AOG})}{M_{OPH}} \right]$$

In a 250 mL flask surmounted with a condenser and provided with a magnetized bar, were incorporated 5 g of an AOG/HPO mixture (with a AOG molar fraction $x_{AOG}$) dissolved in 50 mL of THF, as well as IPDI, the mass $m_{IPDI}$ of which was calculated according to the expression above, and finally the DBTDL catalyst (0.1% by mass based on the total mass of the reagents). The flask was immersed in an oil bath heated to 60° C. for 1 to 10 h. Conversion of the IPDI was followed by infrared spectroscopy, by the disappearance of the vibration band of the NCO groups, localized at 2,250 $cm^{-1}$.

Table 5 gathers the values of the molar masses and of the $T_g$ of the obtained linear polyurethanes.

TABLE 5

Molar masses and $T_g$ of the linear polyurethanes AOH/HPO versus the AOG molar fraction (compound D)

| | AOG molar fraction | $M_w$ (g/mol)[a] | $M_w/M_n$ | Tg (° C.)[b] |
|---|---|---|---|---|
| 1 | 100% | 15 600 | 1.8 | 39 |
| 2 | 80% | 14 500 | 1.8 | 32 |
| 3 | 60% | 13 100 | 1.7 | 24 |
| 4 | 40% | 12 900 | 1.6 | 11 |
| 5 | 0% | 13 500 | 1.7 | −36 |

[a]SEC, DMF solvent, PS calibration.
[b]DSC, a ramp from −50° C. to 100° C., 10° C./min.

The values of the molar masses of the AOG/HPO copolymers slightly vary depending on the AOG proportion (compound (D)), the larger one (15,600 g/mol) being obtained for the homopolymer prepared from HPO. This may be explained by the fact that the latter has a more reactive terminal alcohol function.

The thermograms obtained by DSC reveal $T_g$ temperatures comprised from −36 to 39° C. The time-dependent change of the $T_g$ of the linear polyurethanes according to the compound (D) proportion seems to follow a polynomial trend.

Example 8

Synthesis of Copolymers from the Monomer (E) and from the Diol (G)

A series of copolymers were synthesized from the diol (G) and from the monomer (E) synthesized beforehand, and in the presence of IPDI.

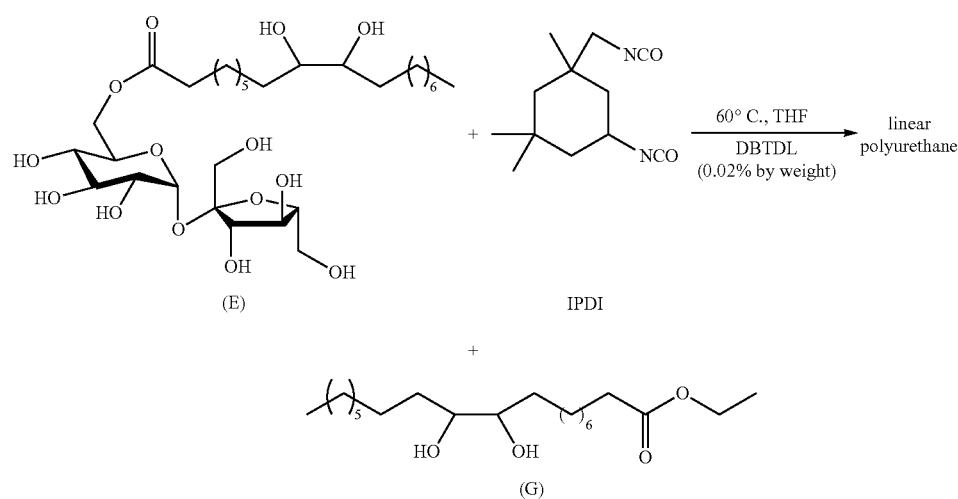

Different polymerization reactions were carried out under the conditions of Example 7.

The following table 6 gathers the results of the polymerizations carried out in THF, for different mass ratios (total duration: 22 h).

TABLE 6

Experimental results of the polymerizations carried out from saccharose and IPDI in THF.

| | (E) ($10^{-4}$ moles) | IPDI ($10^{-3}$ moles) | (G) ($10^{-4}$ moles) | Molar ratio $n_{NCO}/n_{OH}$ | DBTDL (in µL) | Mass composition | Mass Mn/IP |
|---|---|---|---|---|---|---|---|
| 1 | 2.8 | 1.97 | 16.9 | 1 | 0.2 | 25/75 | 2600/1.6 |
| 2 | 5.6 | 1.68 | 11.28 | 1 | 0.2 | 50/50 | 26800/— |

C. Synthesis of Polyurethane Networks from the Monomers

Example 9

Synthesis of a Homopolymer from the Compound (D)

1) Synthesis

The compound (D) was tested as a polyol in the synthesis of novel network polyurethanes in the presence of IPDI.

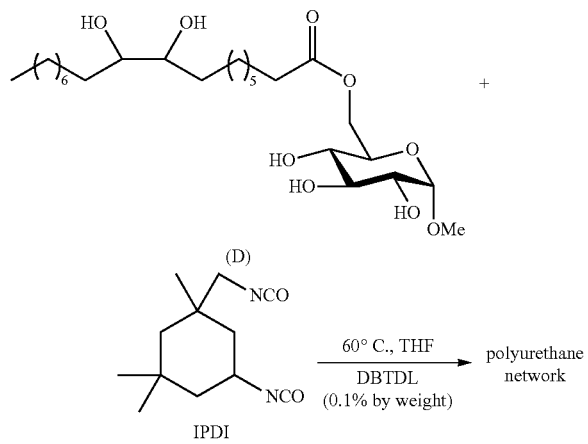

In a 250 mL flask surmounted with a condenser and provided with a magnetised bar, were mixed the compound (D) (5 g; 10.1 mmol) dissolved beforehand in 50 mL of DMF, IPDI (5.61 g; 25.3 mmol) and the DBTDL catalyst (28 mg, 0.1% by mass based on the total mass of the reagents). The flask was then immersed in an oil bath heated to 60° C. After 15 h, the polyurethane was obtained by evaporation of the solvent.

Several polymerization tests were carried out in DMF, which proved to be a good solvent of the compound (D). The following table 7 gathers the results obtained during the polymerizations carried out in the solvent, for different isocyanate function/alcohol function ratios.

TABLE 7

Experimental results of the polymerizations carried out from the compound (D) and IPDI in DMF.

| | Molar ratio $n_{NCO}/n_{OH}$ | Duration of the reaction[a] | NCO conversion | Polymer solubility in DMF[b] | Tg (° C.)[c] |
|---|---|---|---|---|---|
| 1 | 1 | 15 h | Total | Insoluble | 149 |
| 2 | 0.7 | 15 h | Total | Insoluble | 99 |
| 3 | 0.5 | 15 h | Total | Insoluble | 69 |
| 4 | 0.2 | 15 h | Total | Insoluble | 35 |

[a]Determined when the vibration band of the isocyanate functions at 2,250 cm$^{-1}$ no longer changes.
[b]Solubility of the polymer in the solvent when the reaction no longer changes.
[c]DSC, ramp from −100° C. to 200° C., 10° C./min.

All the polymerizations conducted for molar ratios varying from 0.2 to 1 lead to total conversion of the isocyanate functions and to the obtaining of insoluble polymers in DMF. This result is logically explained by the entire reactivity of the five alcohol functions in the solvent.

2) Thermomechanical Properties of the Polyurethanes

Characterization of the network polyurethanes by differential enthalpy analysis reveals glassy transition temperatures $T_g$ ranging from 35 to 149° C. for the 3D networks. The thermal properties of the networks may actually be modulated according to the value of the NCO/OH molar ratio which has a direct influence on the density of the network. The glassy transition temperatures then vary from 35° C. for a molar ratio of 0.2 to 149° C. for a molar ratio of 1 (table 7).

Example 10

Synthesis of AOG/HPO (Hydroxylated Pentanol Oleate) Network Copolymers

1) Synthesis

A series of copolymers were synthesized from hydroxylated pentanol oleate (F), from the compound (I)) (AOG) and in the presence of IPDI.

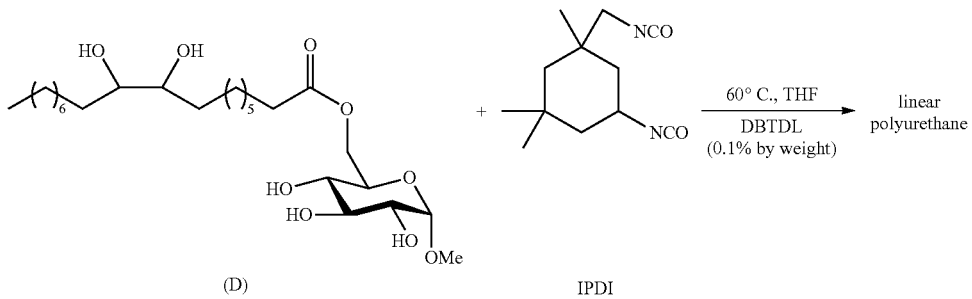

-continued

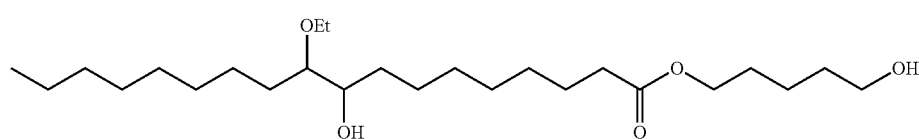

The polymerization reactions were carried out in DMF and IPDI was introduced in a stoichiometric proportion based on the total number of alcohol functions. The AOG/HPO network copolymers were prepared from different AOG molar fractions (compound (D)).

By considering that the molar fraction of AOG incorporated into the mixture of AOG/HPO monomers is $x_{AOG}$ and that the total diol mass is 5 g, then the IPDI mass to be introduced was calculated in the following way:

$$n_{IPDI} = \frac{5}{2[x_{AOG} \cdot n_{AOG} + [(1-x]_{AOG}) \cdot n_{OPH}]} \quad (1)$$

$$m_{AOG} + M_{OPH} = 5 \quad (2)$$

$$(1) + (2) \to m_{IPDI} = \left[ \frac{5 \cdot M_{IPDI}}{2[x]_{AOG}} \cdot \frac{m_{AOG}}{M_{AOG}} + [(1-x]_{AOG}) \cdot \frac{(5-m_{AOG})}{M_{OPH}} \right]$$

In a 250 mL flask surmounted with a condenser and provided with a magnetised bar, were incorporated 5 g of an AOG/HPO mixture (with an AOG molar fraction $x_{AOG}$) dissolved in 50 mL of DMF, as well as IPDI and the DBTDL catalyst (0.1% by mass based on the total mass of the reagents). The flask was immersed in an oil bath heated to 60° C.

2) Thermomechanical Properties of the Network Polyurethanes

The following Table 5 gathers the values of the $T_g$ of the obtained polyurethanes.

TABLE 5

$T_g$ of the AOH/HPO linear polyurethanes versus the AOG molar fraction (compound D).

| | AOG molar fraction | Tg (° C.)[a] |
|---|---|---|
| 1 | 100% | 149 |
| 2 | 80% | 119 |
| 3 | 60% | 91 |
| 4 | 40% | 28 |
| 5 | 20% | −8 |
| 6 | 0% | −36 |

[a]DSC, ramp from −50° C. to 100° C., 10° C./min.

AED analysis of the resulting polyurethanes clearly reveals the influence of the compound (D) on the $T_g$ of the material, the latter increasing linearly with the molar fraction of compound (D). It varies from −36° C. for a compound (D) level from 0% to 149° C. for 100% of incorporated compound (D).

This result is very interesting since it allows access to bio-sourced polyurethane networks having thermomechanical properties which may be modulated.

What is claimed is:

1. A method for preparing polymers selected from polyurethanes and polyesters comprising the step of reacting a first compound with a compound of formula (I):

wherein:

R fits the formula (A):

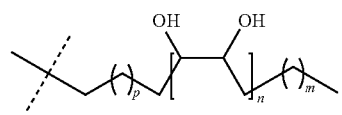

wherein:

n is comprised from 1 to 3;

m is comprised from 1 to 6;

p is comprised from 1 to 9; and

R' is selected from sugars or sugar-alcohols.

2. A compound of formula (I):

wherein:

R fits the formula (A):

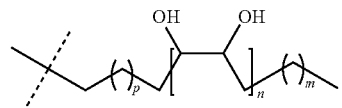

wherein:

n is comprised from 1 to 3;

m is comprised from 1 to 6;

p is comprised from 1 to 9; and

R' is selected from sugars or sugar-alcohols.

3. The compound according to claim 2, wherein R' has one of the following formulae:

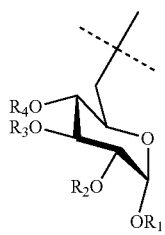

(B)

wherein $R_1$, $R_2$, $R_3$ and $R_4$ represent, independently of each other: H; an alkyl group comprising from 1 to 12 carbon atoms; a group $CH_3C(O)$—; an arylalkyl group comprising from 6 to 12 carbon atoms; a group $((C_1\text{-}C_6)\text{alkyl})_3\text{-Si}$— or $R_1$ and $R_2$, $R_2$ and $R_3$ or $R_3$ and $R_4$, form together an isopropylidene group;

or

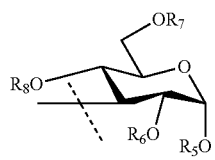

(B')

wherein $R_5$, $R_6$, $R_7$ and $R_8$ represent, independently of each other: H; an alkyl group comprising from 1 to 12 carbon atoms; a group $CH_3C(O)$—; an arylalkyl group comprising from 6 to 12 carbon atoms; a group $((C_1\text{-}C_6)\text{alkyl})_3\text{-Si}$— or $R_5$ and $R_6$ or $R_7$ and $R_8$, form together an isopropylidene group.

4. The compound according to claim 2, wherein R' has the formula (C):

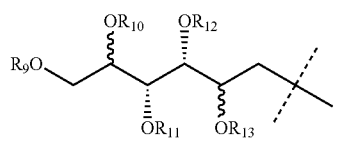

(C)

wherein $R_9$, $R_{10}$, $R_{11}$, $R_{12}$ and $R_{13}$ represent, independently of each other: H; an alkyl group comprising from 1 to 12 carbon atoms; a group $CH_3C(O)$—; an arylalkyl group comprising from 6 to 12 carbon atoms; a group $((C_1\text{-}C_6)\text{alkyl})_3\text{-Si}$— or $R_9$ and $R_{10}$, or $R_{10}$ and $R_{11}$, or $R_{11}$ and $R_{12}$, or $R_{12}$ and $R_{13}$, form together a group isopropylidene.

5. The compound according to claim 2, wherein R' has one of the following formulae:

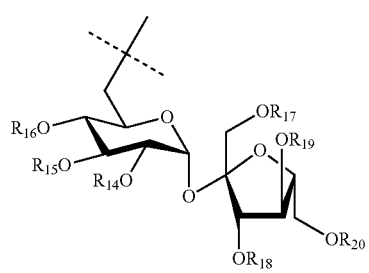

(D)

wherein $R_{14}$, $R_{15}$, $R_{16}$, $R_{17}$, $R_{18}$, $R_{19}$ and $R_{20}$ represent, independently of each other: H; a group alkyl comprising from 1 to 12 carbon atoms; a group $CH_3C(O)$—; an arylalkyl group comprising from 6 to 12 carbon atoms; a group $((C_1\text{-}C_6)\text{alkyl})_3\text{-Si}$— or $R_{14}$ and $R_{17}$ or $R_{19}$ and $R_{20}$ form together an isopropylidene group;

or

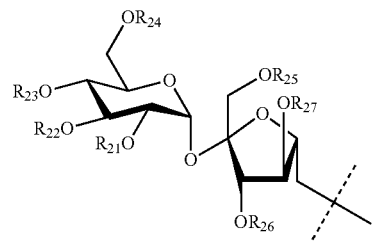

(D')

wherein $R_{21}$, $R_{22}$, $R_{23}$, $R_{24}$, $R_{25}$, $R_{26}$ and $R_{27}$ represent, independently of each other: H; an alkyl group comprising from 1 to 12 carbon atoms; a group $CH_3C(O)$—; an arylalkyl group comprising from 6 to 12 carbon atoms; a group $((C_1\text{-}C_6)\text{alkyl})_3\text{-Si}$— or $R_{23}$ and $R_{24}$ or $R_{21}$ and $R_{25}$ or $R_{26}$ and $R_{27}$ form together an isopropylidene group.

6. The compound according to claim 2, wherein R' has one of the following formulae:

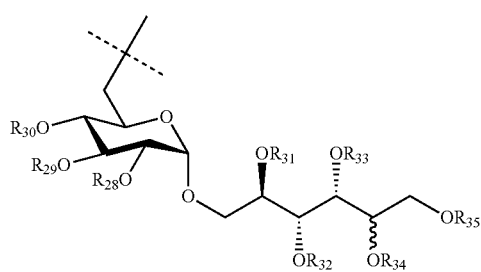

(E)

wherein $R_{28}$, $R_{29}$, $R_{30}$, $R_{31}$, $R_{32}$, $R_{33}$, $R_{34}$ and $R_{35}$ represent, independently of each other: H; an alkyl group comprising from 1 to 12 carbon atoms; a group $CH_3C(O)$—; an arylalkyl group comprising from 6 to 12 carbon atoms; a group $((C_1\text{-}C_6)\text{alkyl})_3\text{-Si}$— or $R_{29}$ and $R_{30}$ or $R_{31}$ and $R_{32}$ or $R_{32}$ and $R_{33}$ or $R_{33}$ and $R_{34}$ form together an isopropylidene group;

or

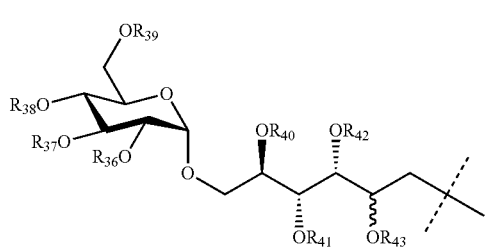

(E')

wherein $R_{36}$, $R_{37}$, $R_{38}$, $R_{39}$, $R_{40}$, $R_{41}$, $R_{42}$ and $R_{43}$ represent, independently of each other: H; an alkyl group comprising from 1 to 12 carbon atoms; a group $CH_3C(O)$—; an arylalkyl group comprising from 6 to 12 carbon atoms; a group $((C_1\text{-}C_6)alkyl)_3\text{-}Si$— or $R_{37}$ and $R_{38}$ or $R_{38}$ and $R_{39}$ or $R_{40}$ and $R_{41}$ or $R_{41}$ and $R_{42}$, or $R_{42}$ and $R_{43}$ form together an isopropylidene group.

7. A polymer which may be obtained by polymerisation of the compound as defined according to claim 2 and of a (poly)isocyanate, notably a diisocyanate fitting the formula $(O)CN\text{-}A_3\text{-}NC(O)$, wherein $A_3$ represents:
 a linear or branched alkyl group, comprising from 2 to 20 carbon atoms; or
 a cycloalkyl-alkyl-cycloalkyl group, comprising from 6 to 30 carbon atoms; or
 an aryl-alkyl-aryl group, comprising from 6 to 30 carbon atoms; or
 a cycloalkyl group, comprising from 3 to 10 carbon atoms;
 an alkyl-cycloalkyl group, comprising from 3 to 15 carbon atoms; or
 an aryl group comprising from 6 to 10 carbon atoms.

8. A polymer which may be obtained by polymerization of the compound as defined according to claim 2, of a diol and of a (poly)isocyanate, notably a diisocyanate fitting la formule $(O)CN\text{-}A_3\text{-}NC(O)$, wherein $A_3$ represents:
 a linear or branched alkyl group, comprising from 2 to 20 carbon atoms; or
 a cycloalkyl-alkyl-cycloalkyl group, comprising from 6 to 30 carbon atoms; or
 an aryl-alkyl-aryl group, comprising from 6 to 30 carbon atoms; or
 a cycloalkyl group, comprising from 3 to 10 carbon atoms;
 an alkyl-cycloalkyl group, comprising from 3 to 15 carbon atoms; or
 an aryl group comprising from 6 to 10 carbon atoms.

9. The polymer according to claim 8, wherein the diol is selected from alkane-diols, polyalkyl-diols, polyether-diols, polyester-diols and diols of the following formulae:

(II)

$R'_1$—(with structure shown: OH, $A_1$, $OR'_2$, C(=O)O$A_2$OH)

wherein:
 $R'_1$ represents a linear or branched alkyl group, comprising from 2 to 14 carbon atoms;
 $R'_2$ represents a linear or branched alkyl group, comprising from 1 to 8 carbon atoms;
 $A_1$ represents a linear or branched divalent radical, comprising from 2 to 14 carbon atoms;
 $A_2$ represents a linear or branched divalent radical, comprising from 1 to 10 carbon atoms;

(III)

HO—(with structure shown: OH, $A'_1$, $R''_1$, C(=O)O$R''_2$)

and
wherein:
 $R''_1$ represents a linear or branched alkyl group, comprising from 2 to 14 carbon atoms;
 $R''_2$ represents a linear or branched alkyl group, comprising from 1 to 8 carbon atoms;
 $A'_1$ represents a linear or branched divalent radical, comprising from 2 to 14 carbon atoms.

10. The polymer according to claim 7, wherein the polymer has the following formula:

[structure shown]

wherein:
 n is 1;
 m is comprised from 1 to 6;
 p is comprised from 1 to 9;
 R' is selected from sugars or sugar-alcohols;
 $A_3$ is selected from the group consisting of:
  a linear or branched alkyl group, comprising from 2 to 20 carbon atoms;
  a cycloalkyl-alkyl-cycloalkyl group, comprising from 6 to 30 carbon atoms;
  an aryl-alkyl-aryl group, comprising from 6 to 30 carbon atoms;
  a cycloalkyl group, comprising from 3 to 10 carbon atoms;
  an alkyl-cycloalkyl group, comprising from 3 to 15 carbon atoms; and
  an aryl group comprising from 6 to 10 carbon atoms;
 q represents an integer comprised from 2 to 500,000.

11. A method for preparing polyurethane, comprising the step for reacting the compound according to claim 8 with a diisocyanate of formula $(O)CN\text{-}A_3\text{-}NC(O)$, according to claim 8, at a temperature comprised from 40° C. to 100° C., in a solvent.

12. A method for preparing polyurethane, comprising the step for reacting the compound according to claim 2, with:
 a diol;
 a diisocyanate of formula $(O)CN\text{-}A_3\text{-}NC(O)$ wherein $A_3$ is selected from the group consisting of:
  a linear or branched alkyl group, comprising from 2 to 20 carbon atoms;
  a cycloalkyl-alkyl-cycloalkyl group, comprising from 6 to 30 carbon atoms;
  an aryl-alkyl-aryl group, comprising from 6 to 30 carbon atoms;
  a cycloalkyl group, comprising from 3 to 10 carbon atoms;
  an alkyl-cycloalkyl group, comprising from 3 to 15 carbon atoms; et
  an aryl group comprising from 6 to 10 carbon atoms;
 at a temperature comprised from 40° C. to 100° C., in a solvent.

13. The method according to claim 11, wherein the solvent is selected from solvents allowing solvation of the compound, in order to obtain a network polyurethane.

14. The method according to claim 11, wherein the solvent is selected from solvents not allowing solvation of the compound in order to obtain a linear polyurethane.

15. The use of the polymers according to claim 7, for vectorization, encapsulation or molecular recognition, notably in the medical, pharmaceutical, cosmetic field; chromatographic separation- or for preparing adhesives, co-surfactants or coatings.

16. The compound according to claim 1, wherein R' is chosen from the group consisting of threose, erythrose, deoxyribose, ribose, xylose, ribulose, lyxose, glucose, methyl glucoside, mannose, fructose, idose, sorbose, galactose, allose, maltose, lactose, isomaltose, isomaltulose, cellobiose, saccharose, raffinose, melezitose, sorbitol, isomalt, xylitol, mannitol and arabinitol.

17. The polymer according to claim 10, wherein q represents an integer comprised from 2 to 50,000.

18. The polymer according to claim 17, wherein q represents an integer comprised from 2 to 5,000.

19. The polymer according to claim 17, wherein q represents an integer comprised from 2 to 50.

20. The method according to claim 11, wherein the temperature is 60° C.

21. The method according to claim 12, wherein the temperature is 60° C.

22. The method according to claim 12, wherein the solvent is selected from solvents allowing solvation of the compound, in order to obtain a network polyurethane.

23. The method according to claim 22, wherein the solvent is DMF or DMSO.

24. The method according to claim 13, wherein the solvent is DMF or DMSO.

25. The method according to claim 12, wherein the solvent is selected from solvents not allowing solvation of the compound, in order to obtain a linear polyurethane.

26. The method according to claim 25, wherein the solvent is THF.

27. The method according to claim 14, wherein the solvent is THF.

28. The method according to claim 1, wherein R represents a linear or branched alkyl group, comprising from 8 to 27 carbon atoms, said alkyl group being substituted with at least two hydroxyl groups and may optionally contain one or more unsaturations.

* * * * *